United States Patent
Uchimura

[11] Patent Number: 5,134,469
[45] Date of Patent: Jul. 28, 1992

[54] ENDOSCOPE LIGHT SOURCE APPARATUS WITH DETACHABLE FLASH UNIT

[75] Inventor: Sumihiro Uchimura, Hachioji, Japan

[73] Assignee: Olympus Optical Co., Ltd., Tokyo, Japan

[21] Appl. No.: 567,527

[22] Filed: Aug. 15, 1990

[30] Foreign Application Priority Data

Nov. 16, 1989 [JP] Japan ................... 1-299996
May 24, 1990 [JP] Japan ................... 2-136044
Jul. 23, 1990 [JP] Japan ................... 2-196723

[51] Int. Cl.⁵ ............................................. H04N 7/18
[52] U.S. Cl. ............................. 358/98; 362/8; 128/6
[58] Field of Search ............. 358/98, 211; 128/6; 362/8, 226; 354/62

[56] References Cited

U.S. PATENT DOCUMENTS

| | | | |
|---|---|---|---|
| 4,464,608 | 8/1984 | Pilley | 354/62 |
| 4,478,212 | 10/1984 | Asano | 128/6 |
| 4,519,684 | 5/1985 | Francis, Jr. et al. | 354/62 |
| 4,803,550 | 2/1989 | Yabe et al. | 358/98 |
| 5,023,639 | 6/1991 | Ushiro et al. | 362/8 X |

FOREIGN PATENT DOCUMENTS

63-314980 12/1988 Japan.

Primary Examiner—Victor R. Kostak
Attorney, Agent, or Firm—Armstrong & Kubovcik

[57] ABSTRACT

A light source apparatus body includes a lighting device for supplying to a light source electric energy required to light up the light source and thereby supply light to an endoscope for normal observation, and a control circuit for controlling the operation of the lighting device. A flash unit supplies to the light source electric energy required to flash it. The flash unit can be detachably mounted on the light source apparatus body through a connector. A sequence of operations conducted to photograph or image an object when freezing/releasing operation is conducted changes in accordance with connection or disconnection of the flash unit.

35 Claims, 17 Drawing Sheets

*(PRIOR ART)*
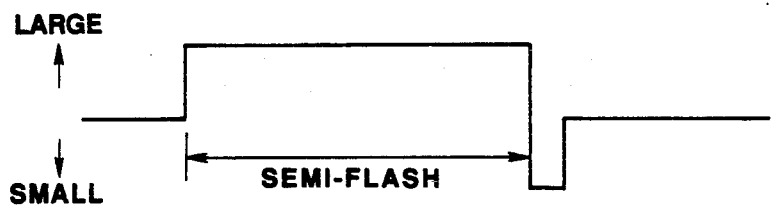
FIG.2a LIGHT INT. (LAMP CURR.)
FIG.2b SHUTTER OF LIGHT SOURCE
FIG.2c SHUTTER OF CAMERA
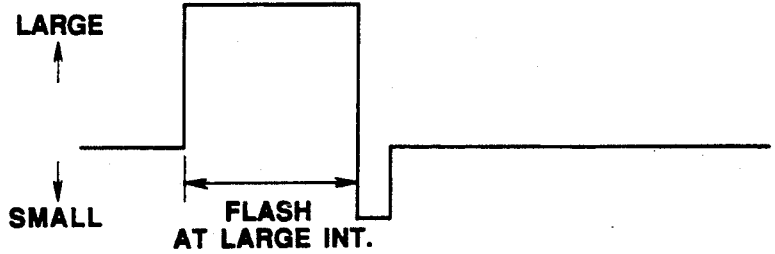
FIG.4a LIGHT INT. (LAMP CURR.)
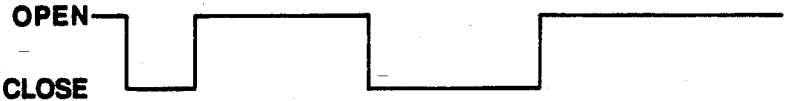
FIG.4b SHUTTER OF LIGHT SOURCE
FIG.4c SHUTTER OF CAMERA

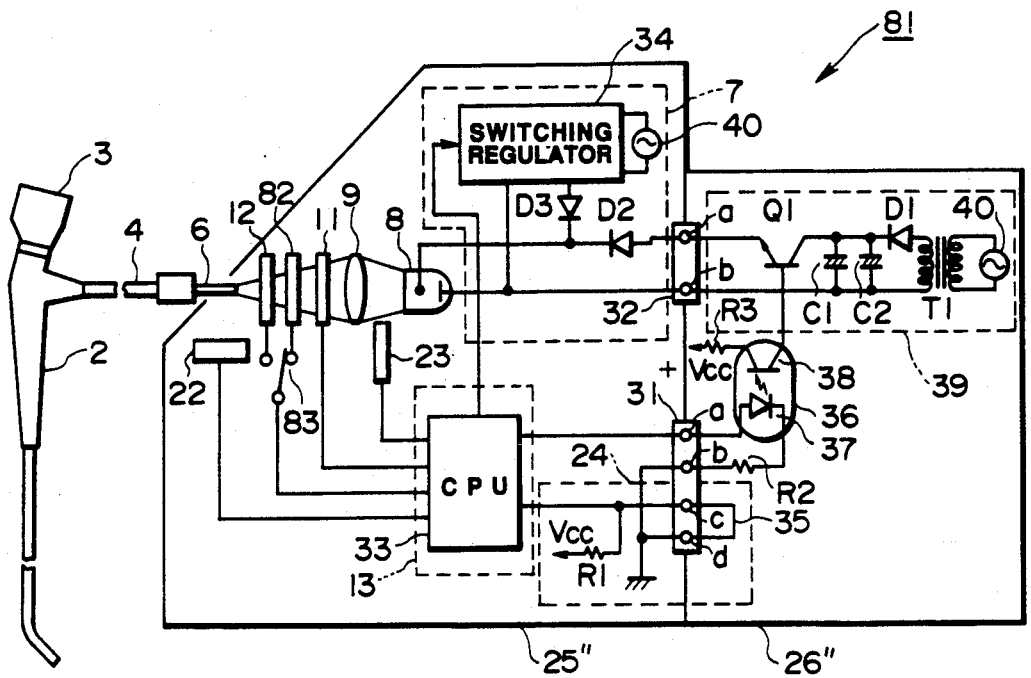

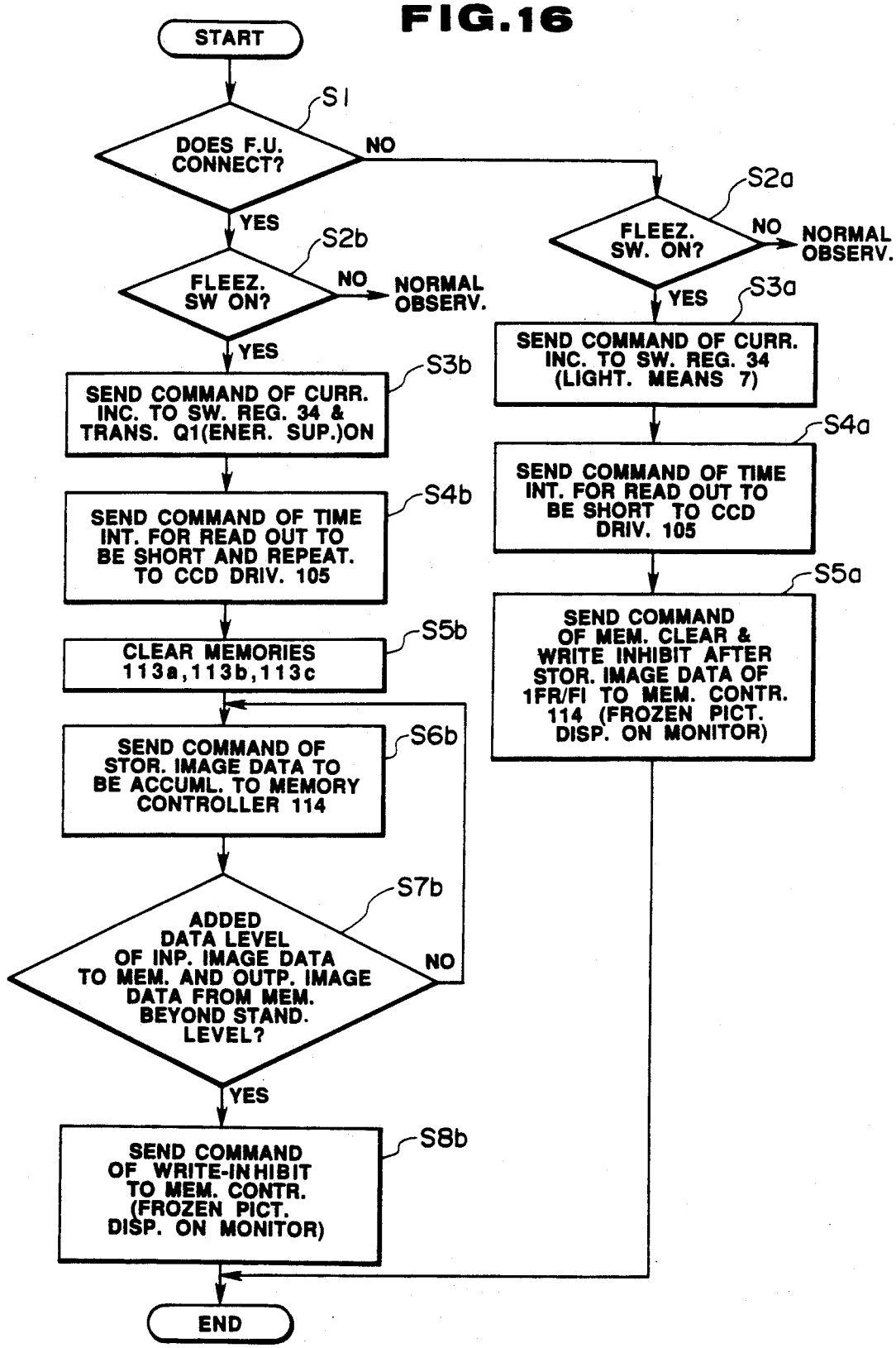

FREEZ. SIG. $\overline{FR}$

READ-OUT PULSE $\overline{DR}$

MEMORY WR. SIG. $\overline{WR}$

LIGHT INT. OF LAMP

FREEZ. SIG. $\overline{FR}$

READ-OUT PULSE $\overline{DR}$

MEMORY WR. SIG. $\overline{WR}$

LIGHT INT. OF LAMP

LIGHTN. SIG. LS

FLASH. SIG. FS

FLASH CON. SIG. FCS

OUTPUT OF SW. SOUR. 312a

OUTPUT OF SW. SOUR. 312b

CURR. APP. TO LAMP

ENDOSCOPE LIGHT SOURCE APPARATUS WITH DETACHABLE FLASH UNIT

BACKGROUND OF THE INVENTION

1. Field of the Invention

The present invention relates to an endoscope light source apparatus with a detachable flash unit

2. Description of the Related Art

In recent years, endoscopes have been widely used not only in the medical field but also in industrial fields.

In order to take pictures of an image observed by the endoscope and sent through an image guide of the endoscope, the light source apparatus of the endoscope generally includes an exposure adjustment means for adjusting an exposure and a control means for controlling the exposure adjustment means. The light source apparatus of this type has a special sequence of photographic operations.

FIG. 1 shows a conventional example of a general photographic system 1 of images observed by the endoscope.

A still camera 3 is mounted on an eyepiece unit of an endoscope (hereinafter referred to as "a scope") 2. The light of a light source apparatus 5 can be supplied to an end surface of a light guide 6 by connecting the end of a light guide cable 4 extending from an operation unit of the scope 2 to a light source apparatus 5.

That is, the light of a lamp 8 which serves as a light source and which flashes by power supplied from a lighting means 7 is condensed by a lens 9, and the amount of condensed light is then adjusted by a stop 11 before it reaches the incident end surface of the light guide 6.

A shutter 12 is detachably provided in an optical path between the stop 11 and the end surface of the light guide 6. Mounting and removal of the shutter 12, together with the aperture of the stop 11, are controlled by a photographic control means 13.

The photographic control means 13 also controls the lighting means 7.

The system 1 can be operated in either the automatic exposure control mode or the manual exposure control mode. In the automatic exposure control mode, when the release operation is performed, the shutter 12 is closed first, as shown in FIG. 2 b, and thereby blocks the light from being sent to the scope 2. At the same time, a shutter of the camera 3 is opened, as shown in FIG. 2 c. Thereafter, the shutter 12 is opened and, at the same time, the amount of light emitted from the lamp 8 is increased by the photographic control means 13 through the lighting means 7, as shown in FIG. 2a, and semi-flashing of the lamp 8 is thereby attained. While the lamp 8 is maintained in the semi-flash state, the photographic control means 13 determines whether or not correct exposure is reached on the basis of the signal sent from a photometric means (not shown) of the camera 3. Once the correct exposure is reached, the photographic control means 13 closes the shutter 12 and at the same time, through the lighting means 7, suspends semi-flashing of the lamp 8, drops the flashing level temporarily to prevent rear marks and then brings it back to a normal flashing level.

Subsequently, the shutter in the camera 3 is closed and the shutter 12 is opened.

Series of these operations are controlled by the photographic control means 13.

In the manual exposure control mode, the same operations are performed as those in the automatic exposure control mode with the exception that the shutter closes when a preset exposure time is reached even if correct exposure level is not attained.

FIG. 3 shows a photographic system 16 including a light source apparatus 15 with a large capacity flash control means 14.

The photographic system 16 differs from the system 1 shown in FIG. 1 in that, as shown in FIG. 4, the lamp 8 does not semi-flash but flashes at a large intensity by the control of the flash control means 14 when the release operation is performed. In consequence, the time required to attain the correct exposure level is reduced and a less blurred image can thereby be obtained. A cooling fan 17 is provided to prevent burning of the light guide 6 which would occur when the lamp flashes.

When pictures are taken using the light source apparatus 15 provided with the flash control means 14 shown in FIG. 3, exposure time can be reduced, and less blurred images can be obtained. Furthermore, pictures of the objects located at farther positions can be taken. However, the size of the light source apparatus 15 is large, and this is very inconvenient for users who do not need flashing: they cannot readily move the system and the entire system costs much.

Japanese Patent Laid-Open No. 314980/1988 discloses a light source apparatus which is energized by one of power sources when an element shutter is not employed and is energized by a flashing power source when the element shutter is used. This prior technique has the same configuration as that shown in FIG. 3 and thus suffers from the same problem.

SUMMARY OF THE INVENTION

An object of the present invention is to provide an endoscope light source apparatus which is useful when a system is constructed in accordance with an environment in which it is used or conductions under which it is used.

Another object of the present invention is to provide an endoscope light source apparatus which is useful when a system is enlarged.

To achieve these objects, the present invention provides an endoscope light source apparatus which comprises: a light source apparatus body including a light source for supplying illumination light to an endoscope, a lighting means for supplying electric energy to the light source to flash it for at least continuous observation/photographing, and a control means for controlling the operation of the lighting means; and a flash unit including a connector means that can be removably mounted on the light source apparatus body, and flash energy supplying means for supplying electric energy required to flash the light source.

BRIEF DESCRIPTION OF THE DRAWINGS

FIGS. 2a–2c explain the operation of the system of FIG. 1;

FIGS. 4a–4c explain the operation of the system of FIG. 3;

FIG. 11 is a schematic view of a third embodiment of the present invention;

FIGS. 12a-12d explain the operation of a modification of the third embodiment;

FIG. 16 is a flowchart of the operation conducted in freezing operation;

DETAILED DESCRIPTION OF THE PREFERRED EMBODIMENTS

Figure 1:
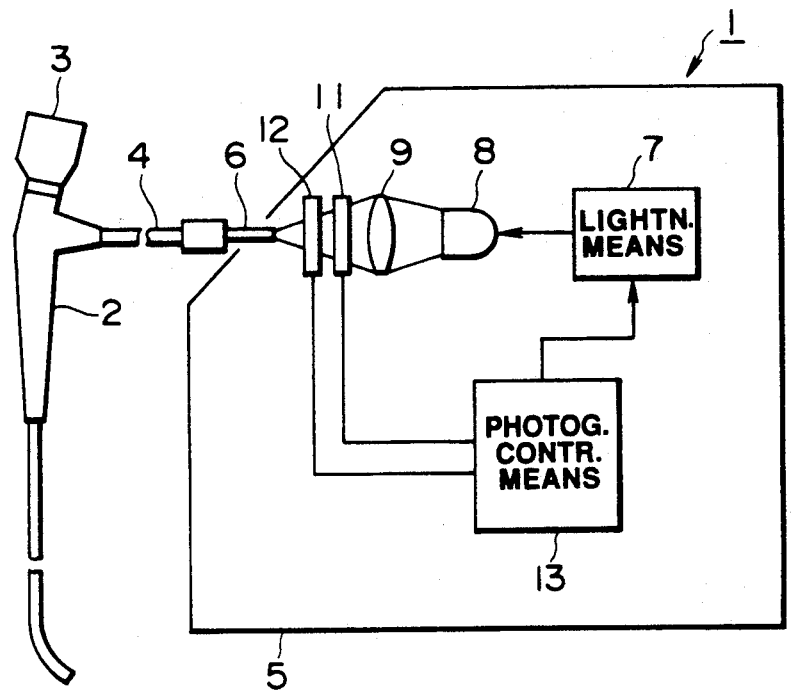
FIG. 1 is a schematic view of a conventional endoscope photographing system.

A first embodiment of the present invention will be described below with reference to FIGS. 5 to 8. In an endoscope photographic system 21 shown in FIG. 5, a light source apparatus 27 includes: a light source apparatus body 25 which contains, in addition to the light source apparatus 5, a cooling fan 22, an attenuating filter 23, and a connection detection means 24; and a flash unit 26 which is removably mounted on the light source apparatus body 25.

In this light source apparatus 27, it is possible to use the light source apparatus body 25 independently as a normal light source apparatus when the flash unit 26 which increases the intensity of light at which the lamp 8 flashes is not necessary. The light source apparatus 27 can also be used as a light source apparatus 27 with the flash unit 26 which provides flashing at a large intensity of light.

The concrete configuration of the light source apparatus 27 will be described below with reference to FIG. 6.

The light source apparatus body 25 has the function of sending light from the lamp 8 to the scope 2 through the lens 9. The light source apparatus body 25 has first and second connectors 31 and 32 which electrically connect the light source apparatus body 25 to the flash unit 26 which has the function of increasing the electrical energy supplied to the lamp 8.

Figure 5:
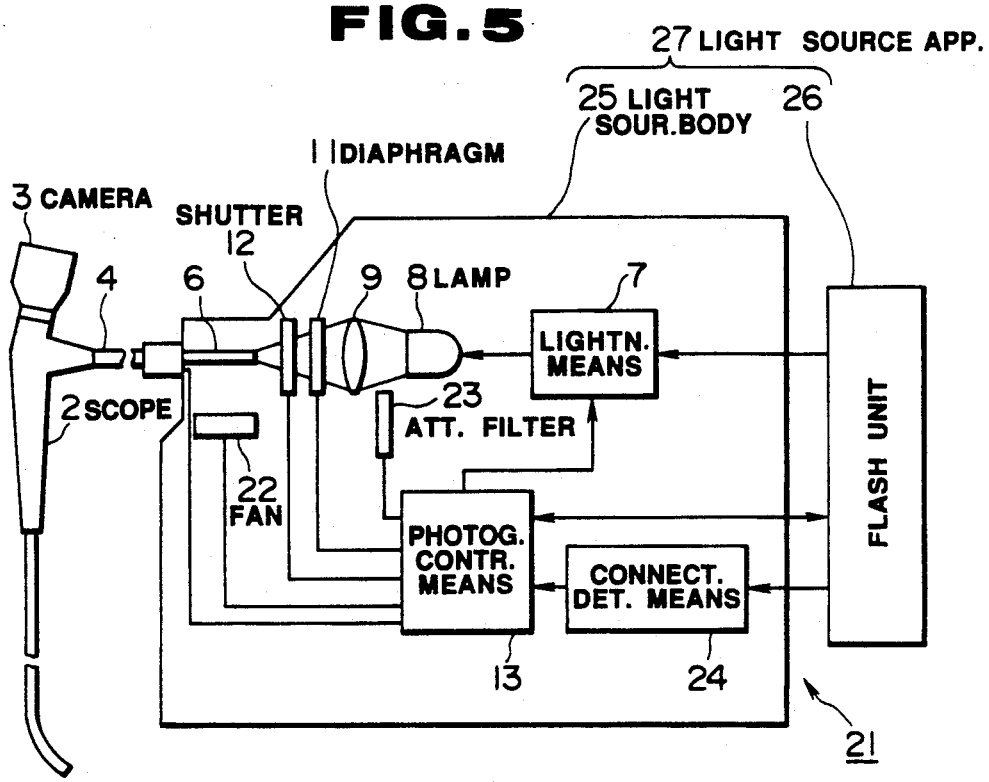
FIG. 5 is a schematic view of an endoscope photographing system, showing a first embodiment of the present invention.

A CPU 33, which constitutes the photographic control means 13 shown in FIG. 5, controls the operation of a switching regulator 34 which constitutes the lighting means 7 that supplies to the lamp 8 electrical energy to flash it. Also, the CPU 33 controls the aperture of the stop 11 which adjusts the amount of light sent to the scope, opening/closing of the shutter 12 which blocks or passes the light in an open state, the operation of the cooling fan 22 which cools the incident portion of the scope 2, and mounting and removal of the attenuating filter 23 which attenuates the light having too large intensity.

The CPU 33 is connected to a pin c of the connector 31 which constitutes the connection detection means 24 and which is also connected to a power source Vcc through a resistor R1. The pin c is at the logical "high" level (hereinafter referred to as "H") when the flash unit 26 is not connected to the light source apparatus body 25. When the flash unit 26 is connected, the pin c is short-circuited to a grounded pin d through a conductor 35, and thereby assumes the logical "low" level (hereinafter referred to as "L").

Thus, the CPU 33 detects connection of the flash unit 26 by determining the level of the pin c.

Also, the CPU 33 is connected to a pin a of the first connector 31, which is short-circuited to a grounded pin b through a LED 37 and a resistor R2 of a photocoupler 36 which is connected to the pin a when the flash unit 26 is connected to the light source apparatus body 25.

A collector of a photo transistor 38 of the photocoupler 36 incorporated in the flash unit 26 si connected to a power source Vcc through a resistor R3, and an emitter thereof is connected to a base of a transistor Q1 which constitutes a flash driving circuit 39.

In this flash driving circuit 39, power of an alternating power source 40 connected to a primary coil of a transformer T1 is transformed to a secondary coil of the transformer due to the electromagnetic induction. The induced current is rectified by a rectifying diode D1 and then stored in parallel-connected capacitors C1 and C2. The positive poles of the capacitors C1 and C2 are connected to a pin a of the second connector 32 through a collector and an emitter of the switching transistor Q1, and negative poles thereof are connected to a pin b of the second connector 32.

The pin a of the second connector 32 is connected to an anode of the light source lamp 8 through a reverse current preventing diode D2, and the pin b thereof is connected to a cathode of the lamp 8.

The anode of the lamp 8 is connected to a positive output terminal of the switching regulator 34 through a reverse current preventing diode D3. Also, the cathode of the lamp 8 is connected to a negative output terminal of the switching regulator 35. The switching regulator 34 is supplied with alternating power from an alternating power source 40.

Upon receipt of an output signal from a photometric sensor 55 incorporated in the camera 3 (when the light guide cable is connected to the light source apparatus body 25), the CPU 33 performs integration of the input signal and thereby determines whether or not correct exposure is attained.

The configuration of the scope 2 and camera 3 will be described below with reference to FIG. 7.

The fiber scope 2 includes a thin inserted unit 41, a thick operation unit 42 connected to the rear end (proximal end) of the inserted unit 41, an eyepiece unit 43 provided at the rear end of the operation unit 42, and a light guide cable 4 extending outwardly from the side of the operation unit 42.

The light guide 6 which is constituted by a fiber bundle passes through the inserted unit 41. The light guide 6 also passes through the operation unit 42 then into the light guide cable 4. The light of the lamp 8 is supplied to the end surface of the light guide 6 when a connector 44 disposed at the end of the light guide cable 4 is connected to the light source apparatus body 25. The light, which is incident to the end surface of the light guide 6, is transmitted to the distal end surface of the inserted unit 41 through the light guide 6 to illuminate an object.

An image of the illuminated object is formed on the focal point surface of an objective lens 46 provided at a distal end portion 45 of the inserted unit 41. An image guide 47 which is constituted by a fiber bundle is disposed such that the distal end surface thereof faces the focal point surface of the objective lens 46 so as to transfer an optical image to the end surface thereof located close to the eyepiece unit 43. An eyepiece 48 is disposed such that it faces this end surface of the image guide 47, and this allows the operator to observe with the naked eye in an enlarged fashion through the eyepiece 48 the transferred optical image.

The (still) camera 3 can be removably mounted on the eyepiece unit 43.

In this camera 3, an image forming lens 51 is disposed opposite to the eyepiece 48. A beam splitter 52 is disposed on the optical axis of the image forming lens 51. The light, which passes through the beam splitter 52, passes through a shutter 53 and then reaches a film 54. The light, which is reflected by the beam splitter 52, is introduced to a photometric sensor 55.

When a release switch 56 is turned on, the shutter 53 retracts from the optical path and thereby passes the light from the beam splitter 52 to the film 54. At that time, a release signal is output and sent to the CPU 33 incorporated in the light source apparatus body 25 through a signal line 57 in the fiber scope 2. Upon receipt of the release signal, the CPU 33 outputs to an output current control terminal 34C of the switching regulator 34 a control signal to increase its output current, and then controls the shutter 12 such that it blocks the light of the lamp 8.

The shutter 53 of the camera 3 is opened substantially in the same timing in which the shutter 12 in the light source apparatus body 25 is closed.

After the shutter 12 has been closed, the CPU 33 outputs a control signal which starts the photometric operation of a photometric circuit 58. This photometric circuit 58 receives an output of the photometric sensor 55 through a signal line 59. The photometric circuit 58 is constituted by an integrating circuit, and starts integration of the photometric signal when the control signal falls and a switch SW thereby turns off. The output of the photometric circuit 58 is applied to one of input terminals of a comparator 62 which constitutes a correct exposure determination circuit 61. To the other input terminal is applied a reference voltage Vs which corresponds to the correct exposure. The comparator 62 outputs a integration completion signal, i.e., an exposure suspension signal, to the CPU 33 when the output level of the photometric circuit 58 exceeds this reference voltage Vs. Upon receipt of this signal, the CPU 33 outputs to the switching regulator 34 of the light source apparatus unit 25 a control signal which reduces the light intensity of the lamp 8 and to the shutter 12 a control signal which closes the shutter 12. After the shutter 12 has been closed, the shutter 53 of the camera 3 is closed. Thereafter, the shutter 12 is opened again to provide illumination required for a normal observation.

In the case where the flash unit 26 is connected to the light source apparatus body 25, a large current is supplied from the flash unit 26 to the lamp 8 to flash it at a large intensity in synchronism with the opening of the shutter 12.

The operation of the first embodiment will now be described with reference to FIG. 8.

Figure 8:
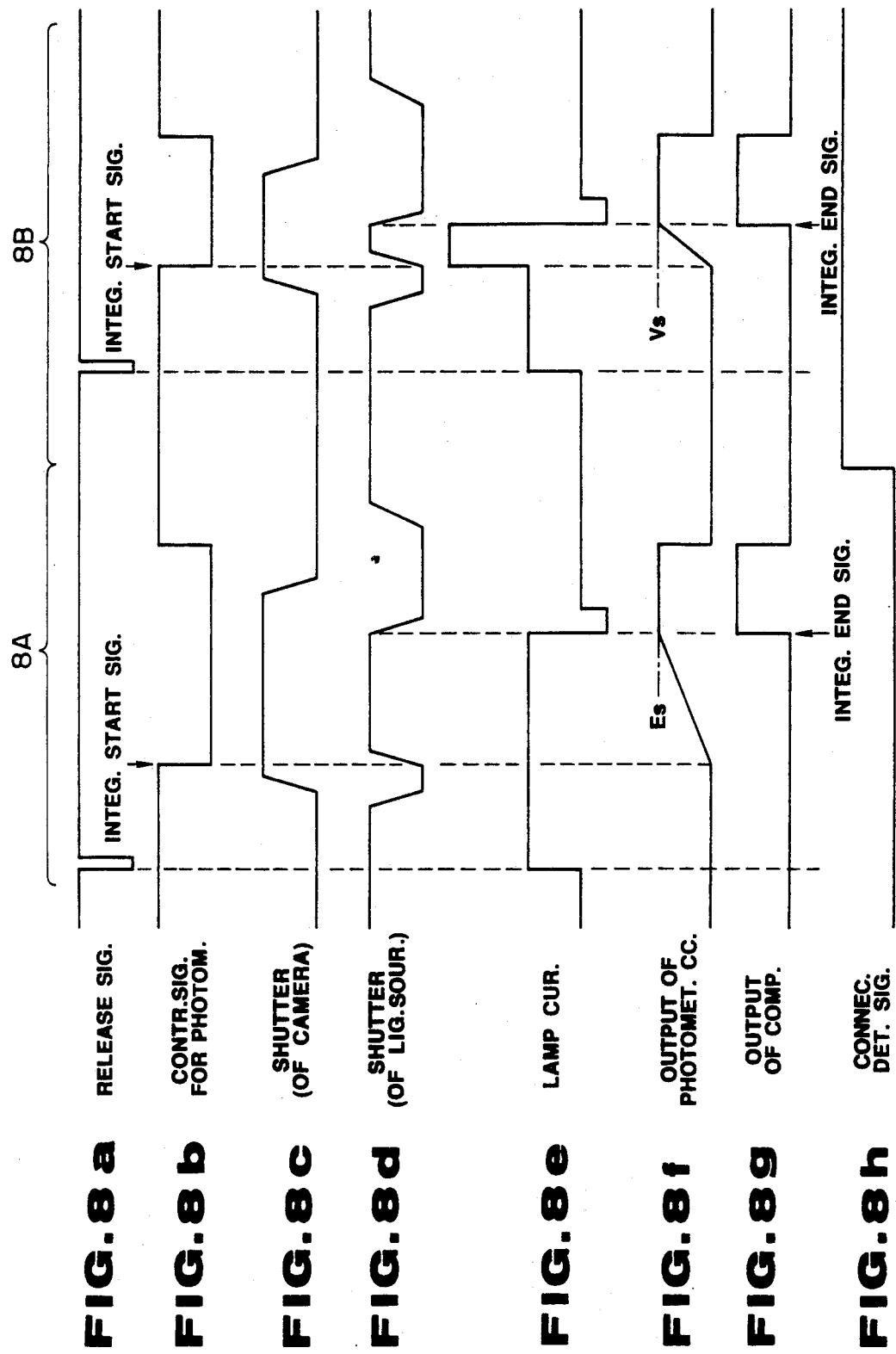
FIGS. 8a-8h is a timing chart explaining the operation of the first embodiment.

In the case where the flash unit 26 is not mounted on the light source apparatus body 25, i.e., where the CPU 33 does not detect the detection signal from the connection detection means 24, the operation of the left half of FIG. 8 (indicated by 8A) is performed by the release operation.

In the normal observation mode, a current of, for example, 18 A, is supplied to the lamp 8 from the switching regulator 34. Once the release switch 56 is turned on, a release signal shown in FIG. 8 a is output and sent to the CPU 33. Upon receipt of this release signal, the CPU 33 increases the lamp current to, for example, 25 A, as shown in FIG. 8 e, to provide semi-flashing of the lamp 8. Thereafter, the CPU 33 temporarily closes the shutter 12, as shown in FIG. 8 d, and substantially at the same time, opens the shutter 52 of the camera 3, as shown in FIG. 8 c.

After the shutter 42 has been opened, the CPU 33 outputs a control signal shown in FIG. 8 b to open the shutter 12 and to start the photometric operation of the photometric circuit 58, i.e., opens a switch 58a of the photometric circuit 58 so that the output signal of the photometric sensor 55 can be received and integrated by the photometric circuit 58. The output signal of the photometric circuit 58 is proportional to the intensity of light to which the film 54 is exposed, and the level thereof rises as the time elapses, as shown in FIG. 8 f. Once this output signal of the photometric circuit 58 reaches the reference voltage Es, the comparator 62 outputs to the CPU 33 a signal (see FIG. 8 g) which informs of the correct exposure. Upon receipt of this signal, the CPU 33 temporarily closes the shutter 12 and at the same time suspends the semi-flashing of the lamp 8. Thereafter, the CPU 33 closes the shutter 53 of the camera 3 and then opens the shutter 12 again. Also, the CPU 33 closes the switch 58a of the photometric circuit 58 and makes it ready for a subsequent release operation.

Figure 3:
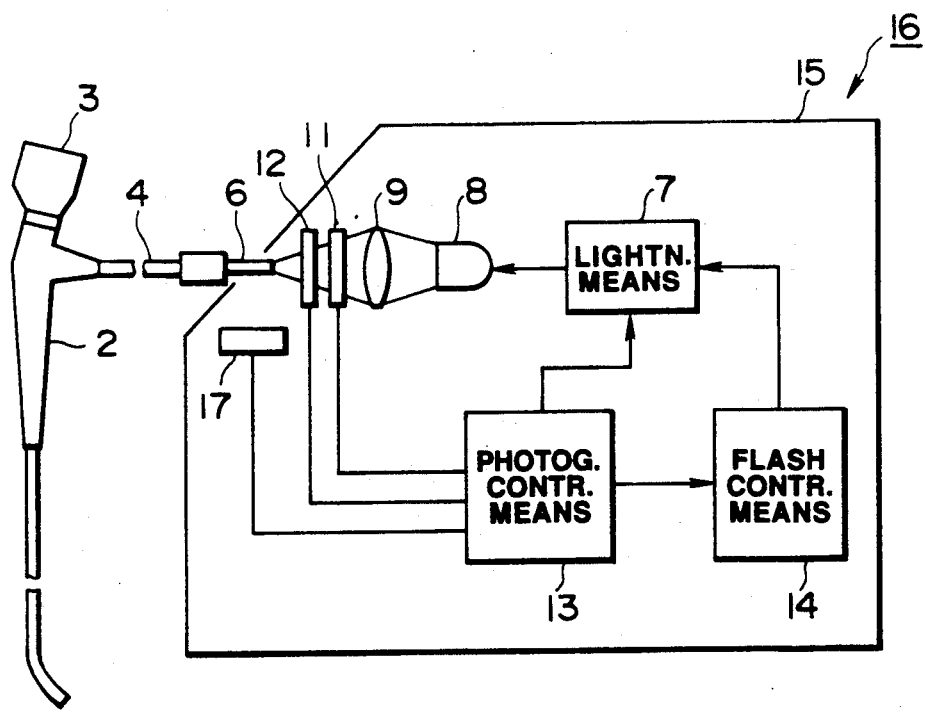
FIG. 3 is a schematic view of another conventional endoscope photographing system.

In the case where the flash unit 26 is connected to the light source apparatus body 25, a sequence of operations indicated by the left half of FIG. 3 (indicated by 8B) are conducted.

Once the flash unit 26 is connected, a connection detection signal shown in FIG. 8 h is sent to the CPU 33. Upon receipt of this signal, the CPU 33 performs the control operation different from that conducted when the flash unit 26 is not connected. That is, after the CPU 33 has increased the current from the switching regulator 34 and has temporarily closed the shutter 12, it turns on the photo transistor 38 in the flash unit 26 and thereby supplies the large electric charges stored in the capacitors Cl and C2 in the flash driving circuit 39 to the lamp 8 through the transistor Q1 in synchronism with the opening of the shutter 12 and starting of the photometric operation.

When the large electric charges stored in the capacitors Cl and C2 are discharged, a large current is supplied to the lamp 8, as shown in FIG. 8 e, to flash it. In consequence, the amount of light to which the film 54 is exposed increases, and the level of the signal detected by the photometric sensor 55 also increases.

Hence, the output of the photometric circuit takes a waveform which rises at a large gradient, as shown in FIG. 8 f, and therefore reaches the reference voltage Vs in a short period of time after the photometric operation (integration) has been started. Once the reference voltage Vs is reached, the comparator 62 outputs a signal to the CPU 33. Upon receipt of the signal, the CPU 33 turns off the photo transistor 38 and thereby suspends flashing of the lamp 8. At the same time, the CPU 33 outputs to the switching regulator 34 a control signal which decreases the output current thereof and closes the shutter 12. The sequence of operations performed thereafter are the same as those in the case where the flash unit 26 is not connected.

In the manual exposure control mode, the exposure time is shorter than that in the normal operation conducted when the flash unit 26 is not connected. Once the set time elapses, the output to the photocoupler 36 (the LED 37) falls to suspend flashing of the lamp 8 at the large intensity, and the shutter 12 closes. The exposure time is made shorter than that in the normal operation so as to attain the same exposure as that obtained in the automatic exposure control mode.

In the first embodiment, when the flash unit 26 is not employed, semi-flashing can be attained. In that case, the overall light source apparatus can be made small in size and can be readily carried from one place to another.

When the flash unit 26 is employed, flashing at a large intensity can be obtained. This provides less blurred photographs. In that case, the correct exposure can be always attained in the automatic exposure control mode. As a result, less blurred photographs of objects located at a distance can be taken.

Furthermore, in the manual exposure control mode, connection of the flash unit is detected, and the exposure time is made shorter than that when the flash unit is connected. In consequence, excess exposure can be eliminated, and the correct exposure can be attained.

In the first embodiment, the light source apparatus can be used in different ways which are suited to an environment in which it is used or conductions under which it is used. For example, when it is desired to obtain less blurred photographs, the flash unit 26 is mounted on the light source apparatus body 25.

In the case where images having a necessary definition can be obtained in a normal observation, the light source apparatus body is used independently.

When it is desired to enlarge the function of an endoscope apparatus (or system) which has been initially constructed by using the light source apparatus body 25 alone, it is not necessary that a new light source apparatus be purchased but only the flash unit 26 is purchased. This is economical.

In the first embodiment, the photocoupler 36 of the flash unit 26 may be replaced by a relay or the like which turns on and off by itself. Furthermore, a photocoupler may be used for detection of the connection.

Figure 9:
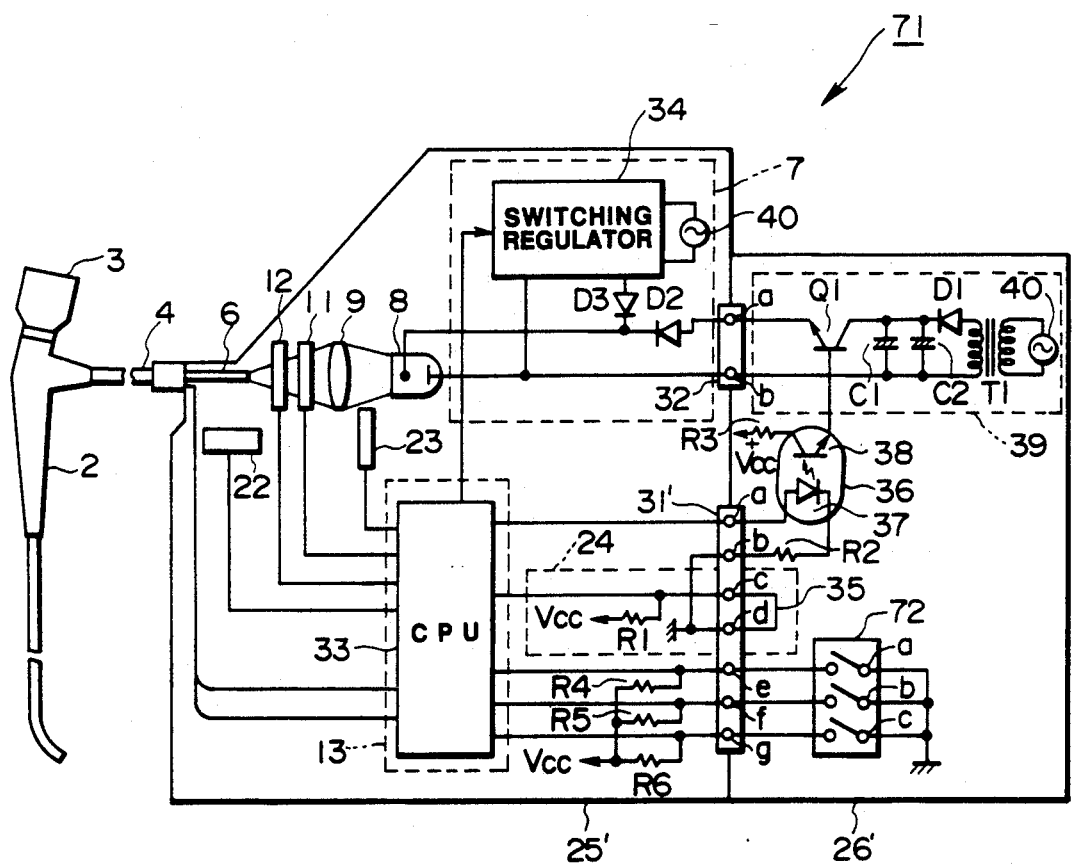
FIG. 9 is a schematic view of a second embodiment of the present invention.
Figure 10A:
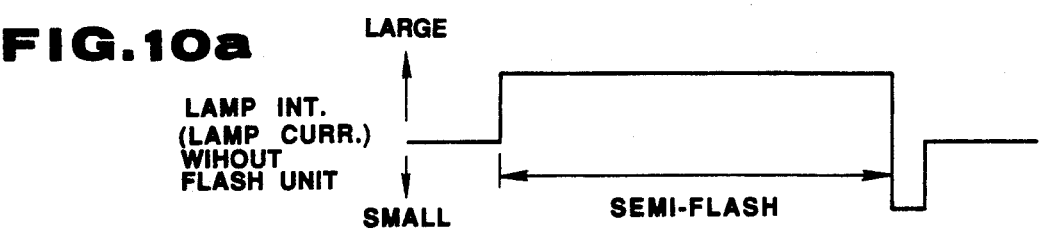
FIGS. 10a-10d explain the operation of the second embodiment.
Figure 10B:
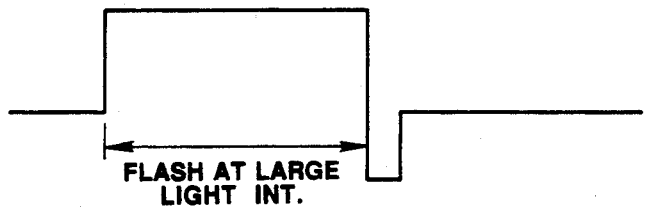
Figure 10C:
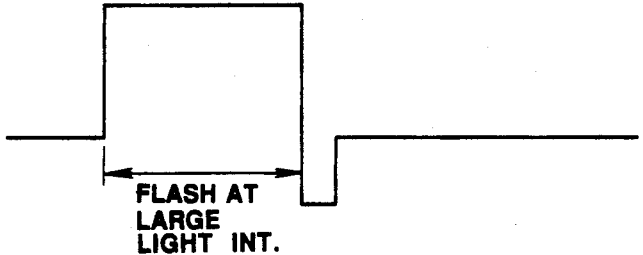
Figure 10D:
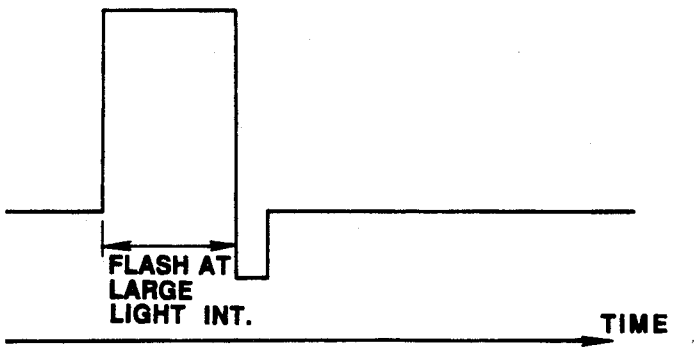

FIG. 9 shows a second embodiment of the present invention.

In this second embodiment, a flash unit 26' of a photographic system 71 has a DIP switch 72 which constitutes an output discrimination means of the flash unit.

That is, a light source apparatus body 25' has a first connector 31' having pins a, b, c, d, e, f and g, and the DIP switch 72 of the flash unit 26' is connected to the pins e, f and g.

The pins e, f and g are connected to the power source Vcc through resistors R4, R5 and R6, respectively. Contacts a, b and c of the DIP switch 72 connected to these pins e, f and g are respectively grounded.

The contacts a, b and c of the DIP switch 72 are turned on and off in response to the amount of energy supplied from the flash unit 26' to the lamp 8. This enables the CPU 33 to determine the actual intensity of light at which the lamp flashes by the detection of the level of the pins e, f and g when the flash unit 26' is connected. In consequence, in the case where the flash unit 26' is connected to the light source apparatus body 25', photographs can be taken in the mode adequate to the intensity of light at which the lamp flashes.

In this second embodiment, the function of the photometric circuit 58 and that of the correct exposure determining circuit 61 are accomplished by the CPU 33.

The operation of the second embodiment will now be described.

The operation of the second embodiment is the same as that of the first embodiment with the exception that, when the flash unit 26' is connected to the light source apparatus body 25', the CPU 33 detects through the pins e, f and g of the connector 31' the output of the DIP switch 72 which is set in accordance with the intensity of light at which flashing is conducted by the flash unit 26' and selects the sequence of photographing operations corresponding to the obtained information from among the sequences of operations which are stored beforehand.

This operation of the second embodiment is shown in FIG. 10.

FIG. 10 a shows the sequence of photographing operations conducted when the flash unit 26' is not connected.

FIGS. 10 b, c and d show the sequences of photographing operations conducted when the flash unit 26' is connected. The sequences of operations shown in FIGS. 10 b, c and d correspond to flash units 26' whose amount of driving energy increases in that order (indicated by 26A, 26B and 26C). As can be seen from FIG. 10, in the case where the flash unit 26' is connected, the higher the intensity of light at which flashing is conducted, the shorter the exposure time. The exposure time in the manual exposure control mode is also in inverse proportion to the intensity of light at which flashing is conducted.

When a large intensity of light is made incident on the light guide 6 of the scope 2 by the connection of the flash unit 26', the temperature of the incident portion of the light guide 6 may rise to an extremely high value at which it burns. Hence, the CPU 33, which detects connection of the flash unit 26' and which discriminates the intensity of light at which flashing is conducted, rotates the cooling fan 22 at a speed corresponding to the intensity of light or operates the attenuating filter 23 when the connected flash unit 26' is one which supplies a certain intensity of light or above.

In the second embodiment, resistors may be employed in place of the DIP switch 72. Furthermore, both the connection detection means and the output discrimination means may be constituted by a single DIP switch. Furthermore, it may also be arranged such that one of a plurality of intensities of light can be selected in a single flash unit. In that case, data representing the selected intensity of light is sent to the CPU, and the CPU selects a sequence of photographing operations which corresponds to the data.

FIG. 11 shows a third embodiment of the present invention.

In a photographing system 81 shown in FIG. 11, a light source apparatus body 25" differs from the light source apparatus body 25 of the first embodiment in that it has two shutters, the shutter 12 and a shutter 82 whose response speed is faster than that of the shutter 12, and in that a switch 82 is provided to switch over these shutters.

In the third embodiment, when the flash unit 26" is connected, the CPU 33 switches over the shutter from the normal shutter 12 to the shutter 82 whose response speed is faster. The other function is the same as that of the first embodiment.

In the third embodiment, the exposure time errors caused by the delay of the response of the shutter can be reduced by using the shutter 82 which responses quickly, and the exposure time can thereby be approximated to the preset value. In consequence, better photographs can be obtained. Particularly, when photographs of closely located objects are taken in the automatic exposure control mode, the actual exposure time can be further approximated to the correct exposure time, so this third embodiment is very advantageous.

When exposure control is performed in the automatic exposure control mode, excess exposure caused by the delay of the shutter 12 may be obtained beforehand, and the CPU 33 may close the shutter 12 when a preset exposure value, which is smaller by the obtained excess exposure, is reached. In the case where a plurality of intensities of light are provided, the CPU 33 may adjust the timing in which the shutter 12 is closed in accordance with the selected intensity of light.

In the second (or third) embodiment, the sequence of operations conducted in the manual exposure control mode when the flash unit 26' (or 26") is connected may be the one shown in FIG. 10. Alternatively, after the release operation is conducted, the lamp 8 may be semiflashed (preflashed at the same level as that in FIG. 12a) by the lighting means 7, as shown in FIGS. 12b, 12c and 12d and then flashed at large intensities of light corresponding to the amounts of driving energy from the flash unit 26'. At that time, the exposure time is varied in accordance with the intensity of flashing light so as to attain the same exposure. In this way, photographs can be taken by the same procedures as those in the normal operation (conducted when no flash unit is connected) regardless of the type of flash unit 26' connected to the light source apparatus body.

The sequences of photographing operations shown in FIG. 12 may also be applied to the first embodiment.

In the above-described embodiments, the sequence of photographing operations conducted to take pictures by means of the camera 3 mounted on the fiber scope 2 differ, depending on the connection or disconnection of the flash unit 26 or 26'.

Next, how the sequence of control operations conducted to obtain an image by the freezing operation or the like changes depending on the connection (mounting) of the flash unit in an endoscope provided with an imaging means will be described below.

Figure 13:
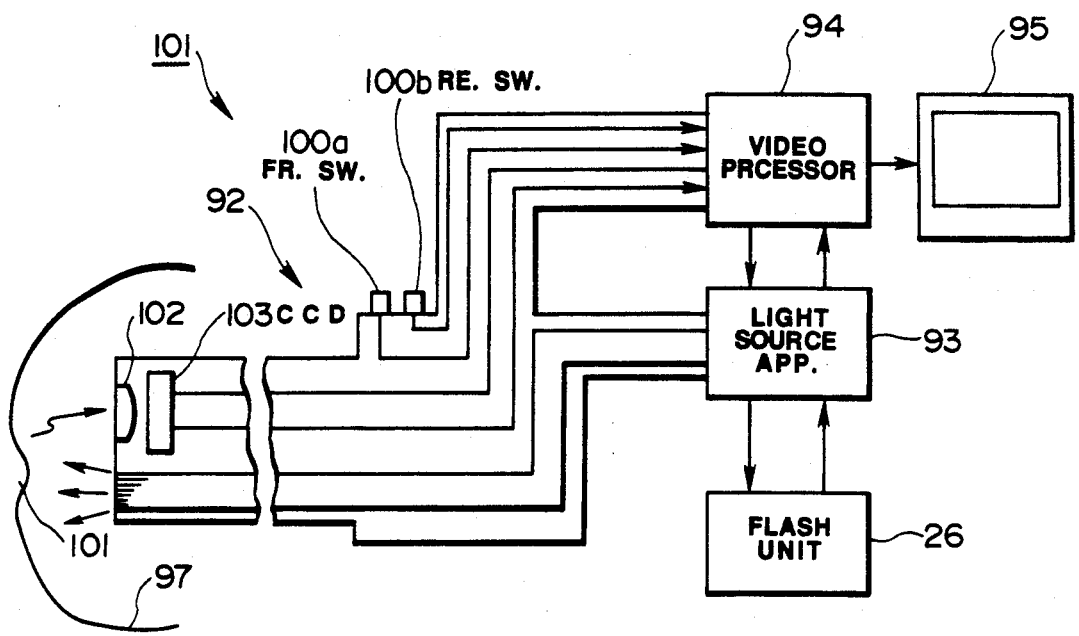
FIG. 13 is a schematic view of an electronic endoscope system, showing a fourth embodiment of the present invention.

FIG. 13 is a schematic view of a fourth embodiment of the present invention.

As shown in FIG. 13, an electronic endoscope system 101 includes an electronic endoscope (hereinafter referred to as "an electronic scope") 92, a light source apparatus body 93 (also called a light source apparatus) for supplying light to the electronic scope 92 for illumination, a video processor 94 for conducting signal processing on the signal output from the electronic scope 92, a monitor 95 for displaying a video signal output from the video processor 94, and a flash unit 26 which can be removably mounted on the light source apparatus 93.

The electronic scope 92 has a thin inserted portion 98 which can be inserted into a cavity 97 or the like. A light guide 99 is passed through the inserted portion 98 to transmit light given to one end surface of the inserted portion 98 which is connected to the light source apparatus 93 to the other end surface thereof and thereby illuminate an object 101. An image of the illuminated object 101 is obtained by an imaging means provided at the distal end of the inserted portion 98. That is, an optical image of the object 101 is formed by an objective lens 102 on the light receiving surface of a CCD 103 disposed on the focal point surface of the objective lens 102

An electrical signal obtained due to the photoelectric conversion by the CCD 103 is input to the video processor 94 where it is processed, and the processed signal is output to the monitor 95 to display it.

The electronic scope 92 has a freezing switch 100a and a releasing switch 100b.

Figure 14:
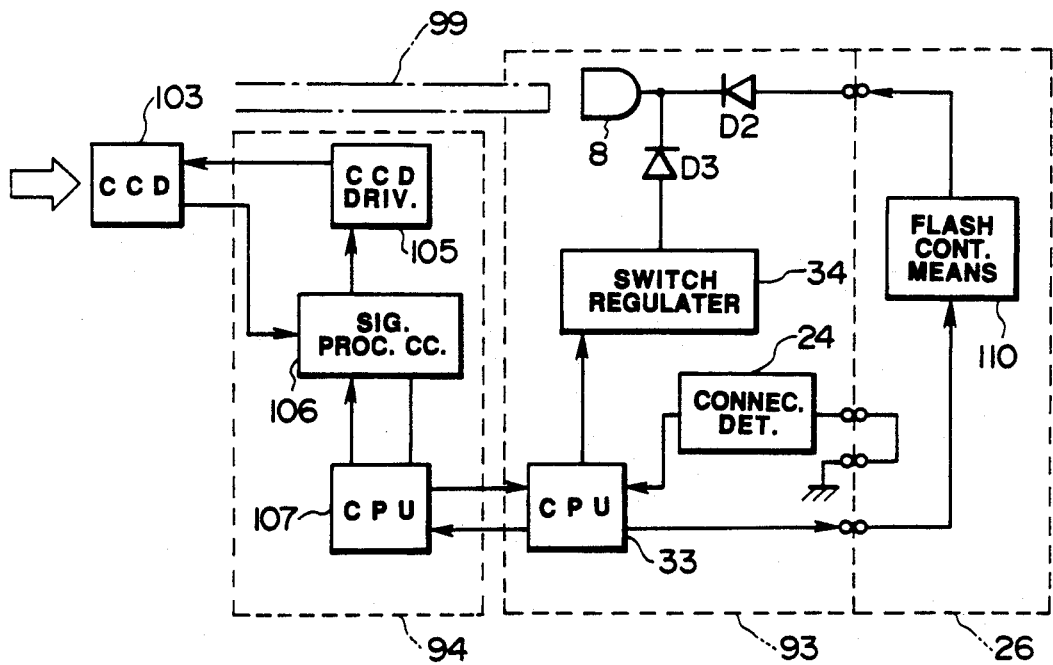
FIG. 14 is a schematic view of an electric system of the fourth embodiment.
Figure 15:
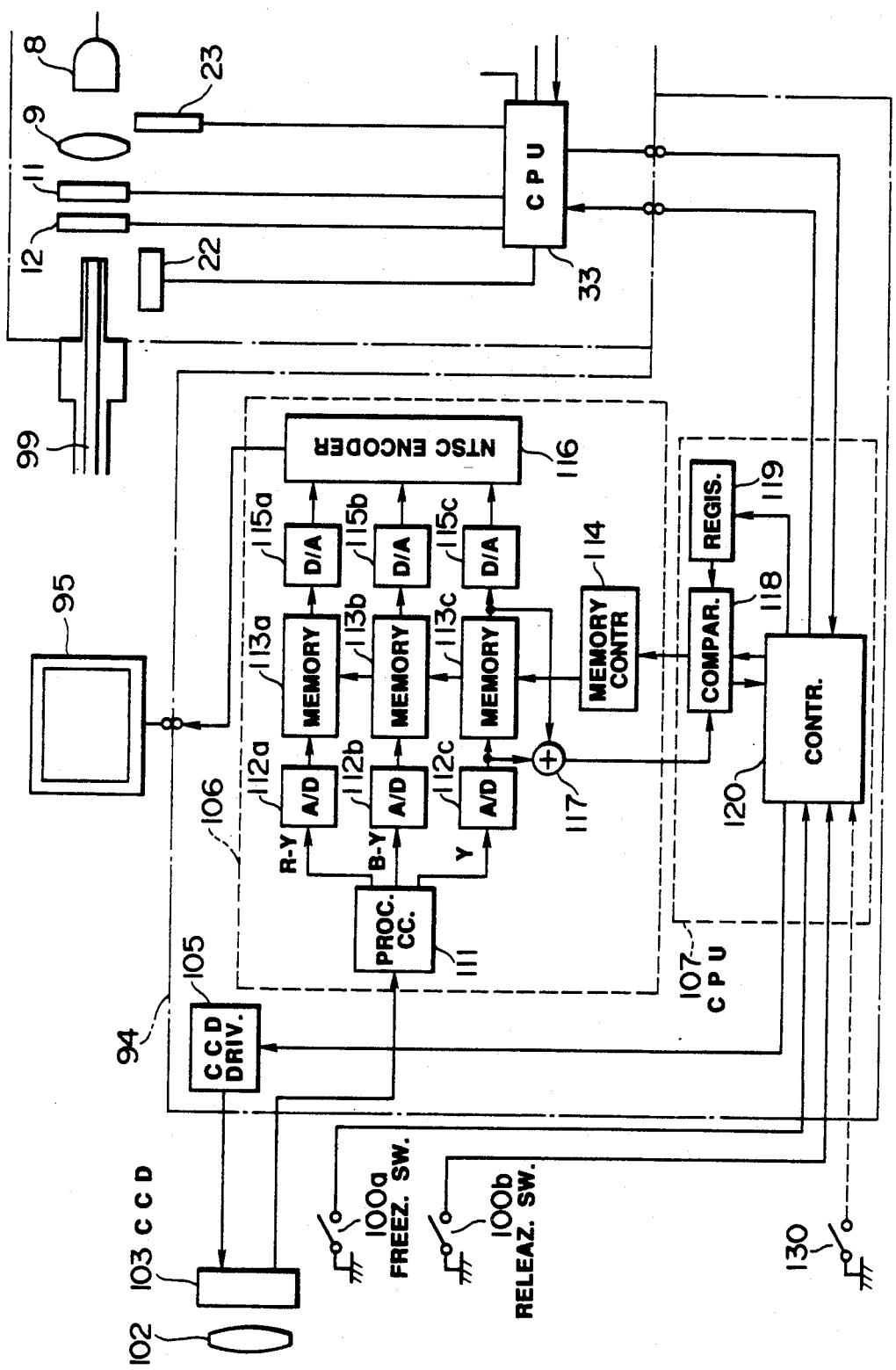
FIG. 15 is a block diagram showing the concrete configuration of a video processor.

FIG. 14 shows the schematic configuration of the video processor 94, and FIG. 15 shows the detailed configuration thereof.

The video processor 94 includes a CCD driver 105 for driving the CCD 103, a signal processing circuit 106 for conducting signal processing on the electrical signal read out from the CCD 13, and a CPU 107 for controlling the signal processing circuit 106 such that it stores a still image signal and for conducting communications with the light source apparatus 93.

Figure 6:
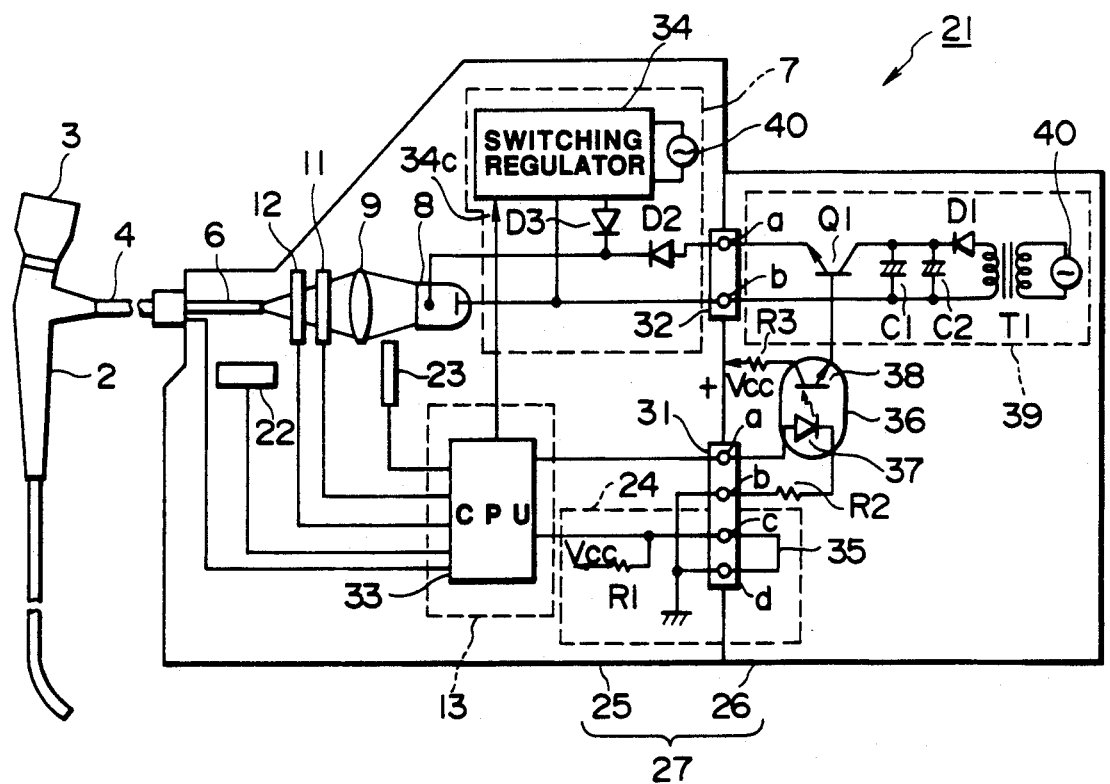
FIG. 6 shows the concrete configuration of a light source apparatus of FIG. 5.

The light source apparatus 93 may have the same configuration as that of the light source apparatus body 25 shown in FIG. 6. In addition to the functions shared by the CPU 33 of the light source apparatus body 25, the CPU 33 of the light source apparatus 93 has the function of conducting communications with the CPU 107 in the video processor 94.

The flash unit 26, which can be detachably mounted on the light source apparatus 93 through the connector means, has the same configuration as that of the flash unit 26 shown in FIG. 6. In FIG. 14, a flash control means 110 has the same function as those of the photo coupler 36 and the flash driving circuit 39 shown in FIG. 6, and is controlled by the CPU 33.

As shown in FIG. 15, an image signal read from the CCD 103 by the application of a CCD drive signal from the CCD driver 105 is delivered to a processing circuit 111 to generate color difference signals R-Y and B-Y and a luminance signal Y.

The signals R-Y, B-Y and Y are respectively converted into digital signals by A/D converters 112a, 112b and 112c, and then stored in memories 113a, 113b and 113c temporarily.

The memories 113a, 113b and 113c are the memory means used to display a still image. Image data is stored (written) in and read out from the memories 113a, 113b and 113c under the control of a memory controller 114. The image data read out from the respective memories are converted into analog signals by D/A converters 115a, 115b and 115c and the converted analog signals are then input to a NTSC encoder 116 to generate a composite video signal. This composite video signal is output to the color monitor 95 which displays an image of the object in color on the screen thereof.

In the fourth embodiment, a still image signal is fetched in intervals shorter than the normal ones when the freezing switch 100a, which is the still image display instruction means, is turned on.

Hence, once the CPU 107 detects a freezing instruction signal which is output when the freezing switch 100a is turned on, it outputs a control signal to the CCD driver 105 to deliver a CCD drive signal to the CCD 103 in short intervals. The image data obtained in short intervals is stored in the memories 113a, 113b and 113c.

In the case where the flash unit 26 is connected to the light source apparatus 93, the CPU 107 further controls such that the still image data stored in the memories 113a, 113b and 113c reaches the correct level.

Hence, the image data to be input to the memory 113c is added to the image data stored in the memory 113c previously by an adder 117, as shown in FIG. 15, and the results of the addition are input to a comparator 118 in the CPU 107 where it is compared with a reference value corresponding to the correct level which is preset in a register 119. The output of the comparator 118 is input to a controller 120 which is activated when the output level of the adder 117 reaches the reference value of the register 119. Once the CPU 107 detects the activation of the controller 120, it outputs to a memory controller 114 a control signal of WRITE-INHIBIT. In the meantime, the image data obtained in short intervals is continuesly accumulated and stored in the memories 113a, 113b and 113c until the control signal of WRITE-INHIBIT is generated.

The operation of the fourth embodiment will now be described with reference to FIGS. 16 to 18.

As shown in FIG. 16, once the system 101 is operated, it is determined in step S1 whether or not the flash unit 26 is connected. This determination is made by the CPU 33 which detects the output level of the connection detection means 24. The results of this determination are transmitted to the CPU 107 of the video processor 94. The light source apparatus 93 and the video processor 94 operate in a sequence determined by the results of the determination. At that time, the light source apparatus 93 increases the intensity of light at which the lamp 8 flashes when the freezing operation is conducted without opening or closing the shutter 12 in the light source apparatus 93, unlike the case where pictures are taken. The lamp 8 semi-flashes when the flash unit 26 is not connected and flashes at a large intensity of light when the flash unit 26 is connected.

If the answer is negative in step S1, it is determined in step S2a whether or not the freezing switch 100a is turned on. The negative answer in step S2a means that the system 10 is in the state in which normal observation is performed. In that case, the CCD drive signal is output in fixed intervals (e.g., 1/60 sec), as shown in FIGS. 17b and 17c, and the signal read out from the CCD by this drive signal is stored in the memory 113 (composed of the memories 113a, 113b and 113c) by the WRITE signal $\overline{WR}$ of the memory controller 114.

Figure 17A:
FIGS. 17a-17d and 18a-18d explain the operation of the fourth embodiment.
Figure 17B:
Figure 17C:
Figure 17D:

Once the freezing (instruction) signal $\overline{FR}$ is sent to the CPU 107 by the operation of the releasing switch 100a, as shown in FIG. 17a, the CPU 107 sends this signal to the CPU 33. Upon receipt of this signal, the CPU 33 sends to the switching regulator 34 of the lightening means 7 a signal to increase an output current in step S3a. In consequence, the lamp 8 semi-flashes, as shown in FIG. 17d. Thereafter, in step S4a, the CPU 107 sends to the CCD driver 105 an instruction to make it output a CCD drive signal having a short period. Also, the CPU 107 sends to the memory controller 114 a control signal to inhibit writing of data in the memory 113 after one frame or field image data obtained in short intervals has been stored in the cleared memory 113 in step S5a. At the same time, the CPU 33 outputs to the switching regulator 34 a control signal to return the output current to a normal value.

The still image data is read out from the memory 113 by WRITE INHIBIT and is displayed on the monitor 95.

Figure 18A:

If it is determined in step S1 that the flash unit 26 is connected, it is determined in step S2b whether or not the freezing switch 100a is turned on. If the freezing switch 100a is turned on, the freezing signal $\overline{FR}$ is output, as shown in FIG. 18a. Once this freezing switch FR is detected by the CPU 107, this is informed to the CPU 33. In step S3b, the CPU 33 outputs to the switching regulator 34 a signal to increase an output current thereof, and at the same time turns on the transistor Q1 of the flash unit 26 through the photo coupler 36 and thereby supplies a large current to the lamp 8 from the flash unit 26. Thus, the lamp 8 flashes at a large intensity of light, as shown in FIG. 18d.

Figure 18B:
Figure 18C:

Substantially in the same timing as the flashing of the lamp 8, the CPU 107 sends to the CCD driver 105 a control signal to output a CCD drive signal in short intervals in step S4b. Thus, the CCD drive signal is output in short intervals, as shown in FIG. 18b, while the lamp 8 is flashing at a large intensity of light. Thereafter, the CPU 107 sends to the memory controller 114 a command and thereby clears the memory 113 in step S5b. Thereafter, the CPU 107 sends to the memory controller 114 a command and thereby cumulatively stores the image data in the memory 113. That is, the image data obtained in short intervals is cumulatively stored in the memory 113. The image data to be stored in the memory 113c is added to the image data stored in the memory 113c by the adder 117, and the results of the addition are input to the comparator 118 of the CPU 107 in sequence. Thereafter, it is determined in step S7b whether or not the image data level reaches the reference level. The image data is continuously accumulated in the memory 113 until the reference level is reached. Once the reference level is reached, the CPU 107 sends to the memory controller 114 a WRITE INHIBIT command in step S8b. The image data whose level is reached to the reference level is retained in the memory 113 by this WRITE INHIBIT command and is read out to the monitor 95 in sequence and displayed as a still image.

Figure 18D:
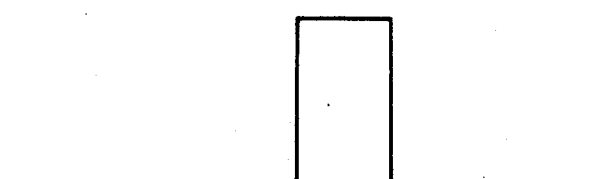

Subsequently, the CPU 33 decreases the output current of the switching regulator 34 and turns off the transistor Q1 of the flash unit 26 through the photo coupler 36 to reduce the lamp current to a value corresponding to the normal observation state, as shown in FIG. 18d.

The thus-obtained still image is less blurred due to short exposure time and accomplishes the correct exposure. For example, an image of the object located at a short distance can be blurred less. An image of the object located at a long distance can be bright.

Furthermore, a still image of an organ, such as the oesophagus or stomach, which is located in the vicinity of the heart and which moves quickly, can be less blurred when it is obtained at a short distance. Also, an image of the entirety of the stomach can be bright when it is obtained at a long distance.

Since the flash unit 26 is a separate component and can be detachably mounted on the light source apparatus 93, if the endoscope system is used in an environment where the flash unit 26 is unnecessary, the cost of the endoscope system can be reduced.

Furthermore, the flash unit 26 may be selectively mounted on any of a plurality of endoscope systems which is used in an environment (state) where mounting of the flash unit 26 is desirable. In this way, the number of flash units 26 employed can be made smaller than the number of endoscope systems.

Even when the flash unit 26 is connected to the light source apparatus 93, if flashing at the large intensity of light is unnecessary, flashing at a large intensity of light may be able to be inhibited by the provision of a switchover switch 130 which is connected to the CPU 107 or the like in the manner shown by the broken line in FIG. 15.

This allows the user to select the type of flashing in accordance with the conditions under which the endoscope is used.

When the releasing switch 100b is operated, preparation for outputting the video signal of a still image is made first, and a signal is then output to a recording apparatus to record the still image, as in the case where the freezing switch 100a is operated. Thus, in the case where the recording apparatus is not connected, the same operation as that conducted in the case where the freezing switch 100a is turned on is conducted.

Figure 19:
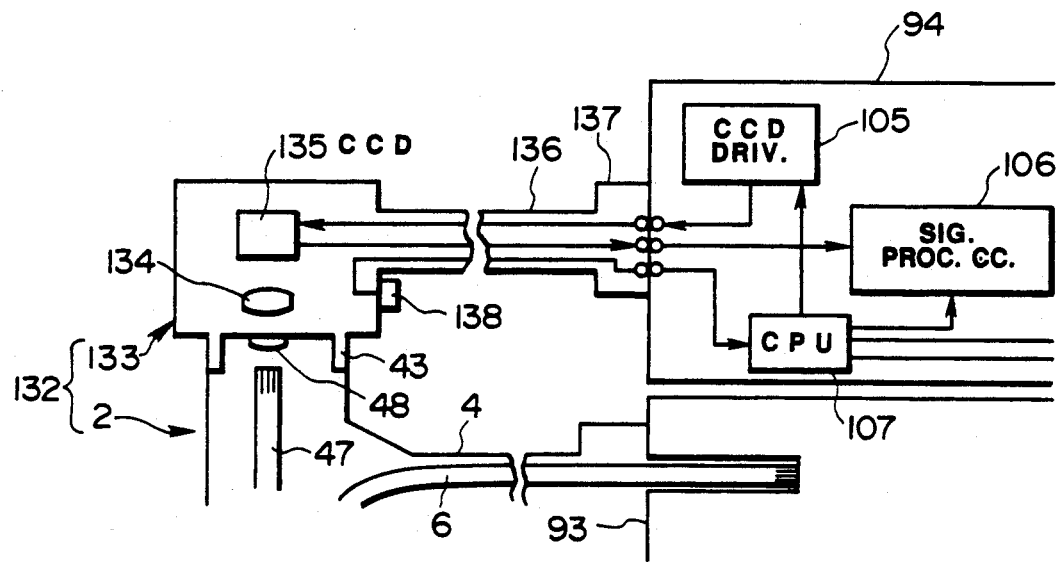
FIG. 19 a schematic view of a TV camera, showing a modification of the fourth embodiment.

FIG. 19 shows a modification of the fourth embodiment of the present invention which is an endoscope 132 with an attached type TV camera.

Figure 7:
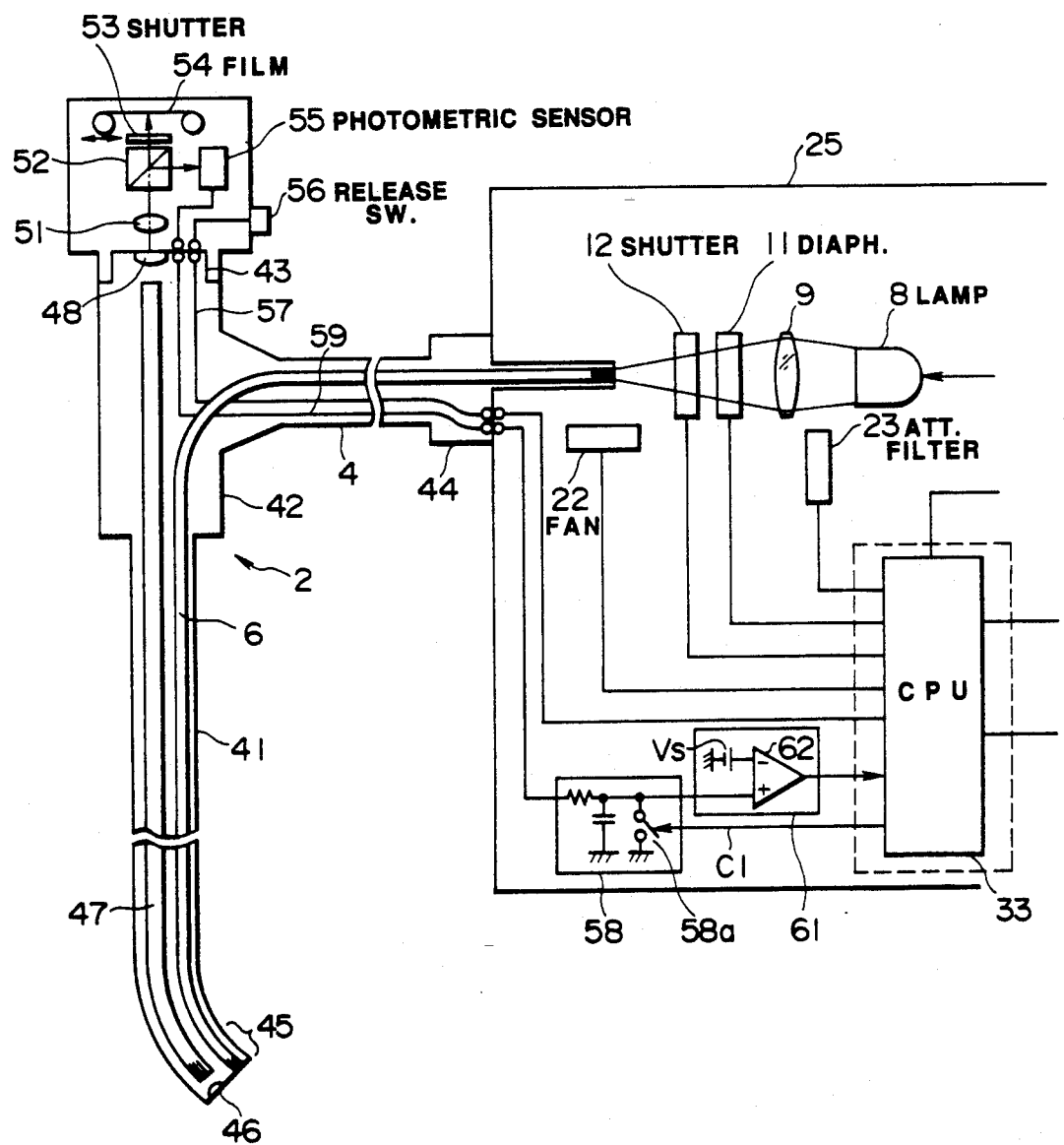
FIG. 7 shows the configuration of a fiber scope and a camera of FIG. 5.

This modification employs in place of the electronic scope 92 employed in the fourth embodiment the fiber scope 2 shown in FIG. 7 with a TV camera 133 attached thereto.

In this TV camera 133, an image forming lens 134 and a CCD 135 are disposed in opposed relation to the eyepiece 48 so that an optical image transmitted through the image guide 47 can be formed on the CCD 135. The CCD 135 can be electrically connected to the CCD driver 105 and to the signal processing circuit 106 by connecting a connector 137 provided at the end portion of a cable 136 extending from the TV camera 133 to the video processor 94. A freezing switch 138 provided on the TV camera 133 is connected to the CPU 107 in the video processor 94 so that a freeze signal $\overline{FR}$ can be transmitted from the freezing switch 138 to the CPU 107.

The operation of this modification is the same as that of the fourth embodiment, description thereof being omitted.

Figure 20:
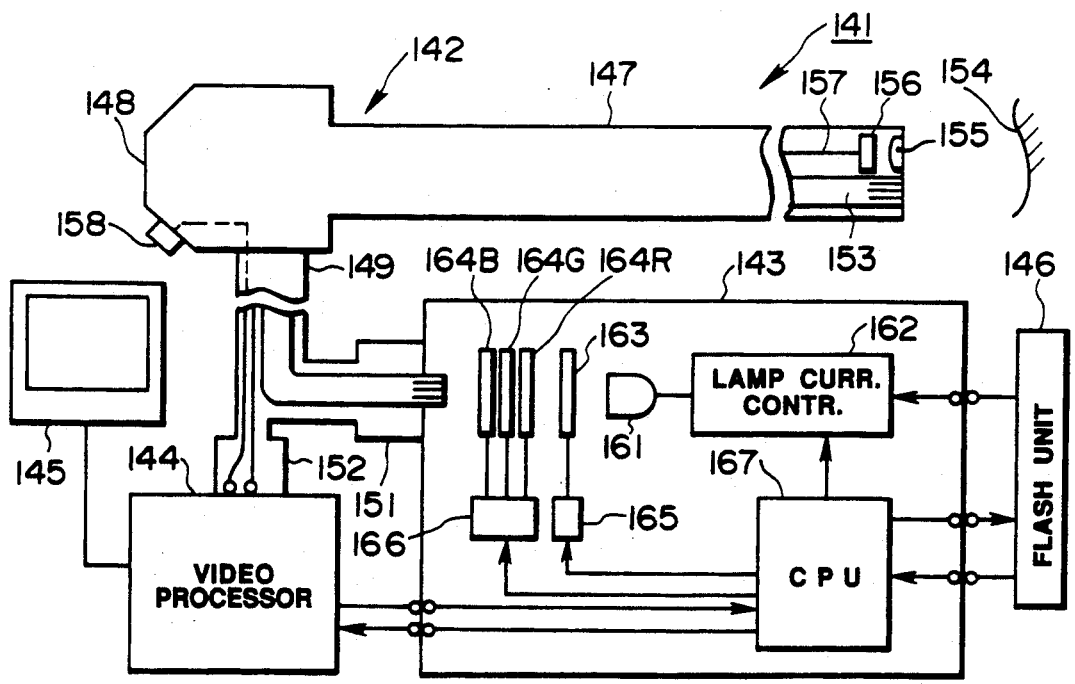
FIG. 20 is a schematic view of a fifth embodiment of the present invention.

FIG. 20 shows a fifth embodiment of the present invention which is a field-sequential electronic endoscope system 141.

The system 141 includes a field-sequential electronic endoscope 142, a light source apparatus 143, a video processor 144, a monitor 145 and a flash unit 146 which can be removably mounted on the light source apparatus 143.

The electronic endoscope 142 includes a thin inserted portion 147, a thick operating portion 148 formed at the rear end of the inserted portion 147, and a universal cable 149 extending from the operating portion 148. The universal cable 149 has at its two ends a light guide connector 151 and a signal connector 152 that can be connected to the light source apparatus 143 and to the video processor 144, respectively.

A light guide 153 is inserted throughout the inserted portion 147 and universal cable 149 so that the light from the light source apparatus 143 can be transmitted to an emitting end surface mounted on the distal end surface of the inserted portion 147 to illuminate an object 154.

An image of the illuminated object 154 is formed on a CCD 156 located on the focal point surface of an object lens 155 by means of the object lens 155 mounted on the distal end of the inserted portion 147, and thereby converted into an electric signal.

The produced signal is read out from the CCD 156 by a drive signal supplied to the CCD 156 from a CCD driver in the video processor 144 through a signal line 157. The read out signal is input to a signal processing system in the video processor 144.

A switch 158 is provided on, for example, the operating portion 148 of the electronic endoscope 142. The switch 158 outputs a still picture displaying signal, i.e., a freeze signal $\overline{FR}$, when it is operated.

A lamp 161 in the light source apparatus 143 flashes due to the lamp driving current from a lamp current control circuit 162. The light from the lamp 151 is supplied to the end surface of the light guide 153 disposed in opposed relation to the optical axis of the light through a stop 163 and a shutter 164R, 164G or 164B with a filter of R, G or B.

The aperture of the stop 163 is controlled by a stop driving device 165. The shutters 164R, 164G and 164B are driven such that they are introduced into and removed from the optical path of the light from the lamp 161 by a shutter driving device 166. The shutters 164R, 164G and 164B are introduced into the optical path in sequence. The shutters 164R, 164G and 164B each have a shutter portion and a filter portion formed adjacent to the shutter portion, and block the light when the shutter portion is located in the optical path and pass the light of red (R), green (G) or blue (B) when the corresponding filter is located in the optical path.

The stop driving device 165 and the shutter driving device 166 respectively drive the stop 163 and the shutters 164R, 164G and 164B under the control of a CPU 167.

The flash unit 146 can be detachably mounted on the light source apparatus 143. Connection or disconnection of the flash unit 146 differs the sequence of operations conducted by the light source apparatus 143 for flashing when the freezing operation is to be conducted and those conducted by the video processor 144 for freezing when the freezing operation is to be conducted. The sequence of operations conducted by both the light source apparatus 143 and the video processor 144 in either case are basically the same as that conducted in the fourth embodiment. That is, with respect to the single flashing and the single CCD reading out pulse DR in the fourth embodiment, flashing is conducted three times and three reading out pulses are output in this fifth embodiment. In other words, the object 154 is illuminated by the light of R, G and B in sequence. Illumination is conducted three times and three reading out pulses are output to obtain a single color image. Hence, in the case where flashing is conducted, flashing is conducted three times, and R, G and B lights are obtained by respectively passing the light of the flashing through the R, G and B shutters 164R, 164G and 164B. The object is exposed by these R, G and B lights in sequence, and the obtained signals are respectively stored in three memories (not shown) in the video processor 144. A CCD signal obtained by exposing the object by a subsequent R light, for example, is cumulatively added to the signal stored in the R memory. Once the obtained level reaches the reference level, writing of data in the memory is inhibited and the stored signal data is output to the monitor 145 and displayed.

The fifth embodiment has the same advantages as those of the fourth embodiment.

Figure 21:
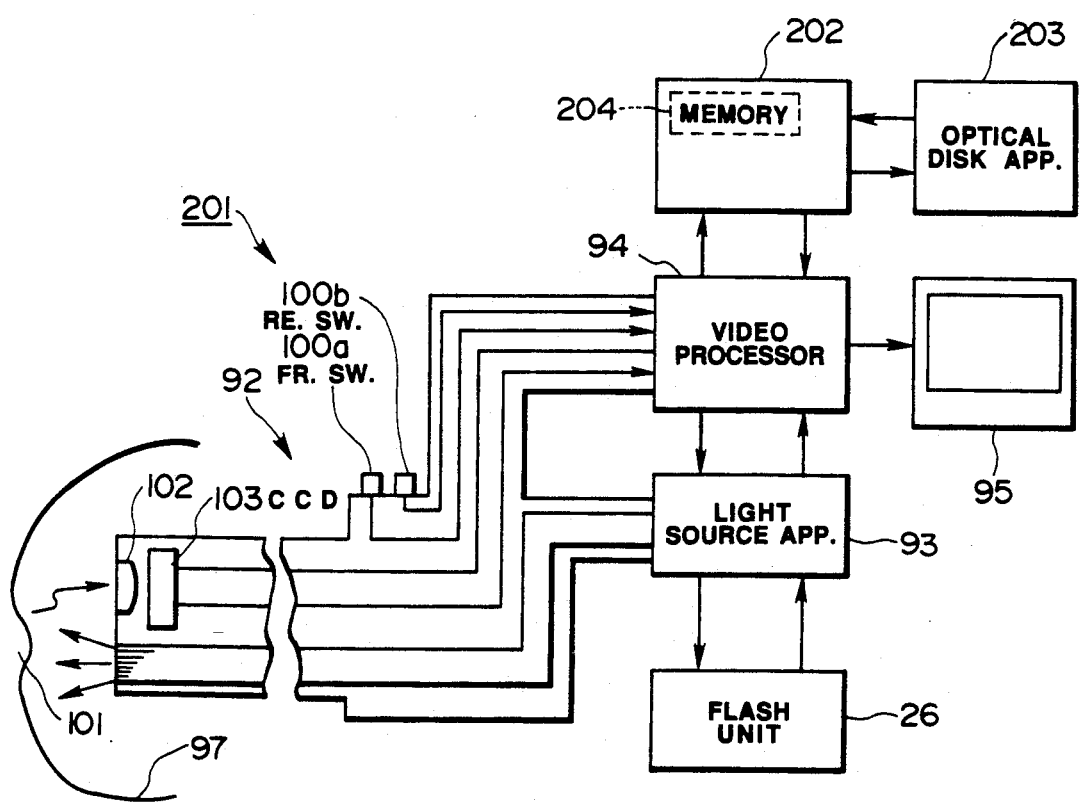
FIG. 21 is a schematic view of a sixth embodiment of the present invention.

FIG. 21 shows a sixth embodiment of the present invention which is an endoscope system 201.

This sixth embodiment differs from the fourth embodiment in that an image file device 202 and an optical disk device 203 are provided.

The image file device 202 is connected to the video processor 94 and receives a video signal and a releasing signal from the video processor 94. The image file device 202 controls recording of still pictures. The image file device 202 is also connected to the optical disk device 203 which records still pictures, and sends to the optical disk device 203 the releasing signal to record a still picture in the optical disk device 203. The images recorded in the optical disk device 203 can be transferred to a memory 204 in the image file device 202 and then output to the monitor 95 through the video processor 94.

The image file device 202 is always in receipt of data corresponding to a single screen from the video processor 94 and is holding it in its memory 204. Thus, the image data corresponding to the single screen can be recorded in the optical disk device 203 by operating a releasing switch (not shown) on the image file device 202.

When the releasing switch 100b of the electronic scope 92 is operated, the still picture data is stored in the memory 113 in the video processor 94, and the stored still picture data is transferred to the memory 204 in the image file device 202 and then recorded in the optical disk device 203.

It may also be arranged such that the image data in the memory 113 is directly recorded in the optical disk device 203 without being passed through the memory 204 in the image file device 202.

It may also be arranged such that the image data recorded in the optical disk device 203 is directly read out to the monitor 95 and displayed without being passed through the memory 204 in the image file device 202.

In this embodiment, less blurred still pictures can be filed in the image file device 203, so still pictures can be stored substantially permanently in a non-deteriorated state.

The optical disk device 203 may be replaced by a recording device which employs an optical magnetic disk, VTR or a magnetic tape.

Figure 22:
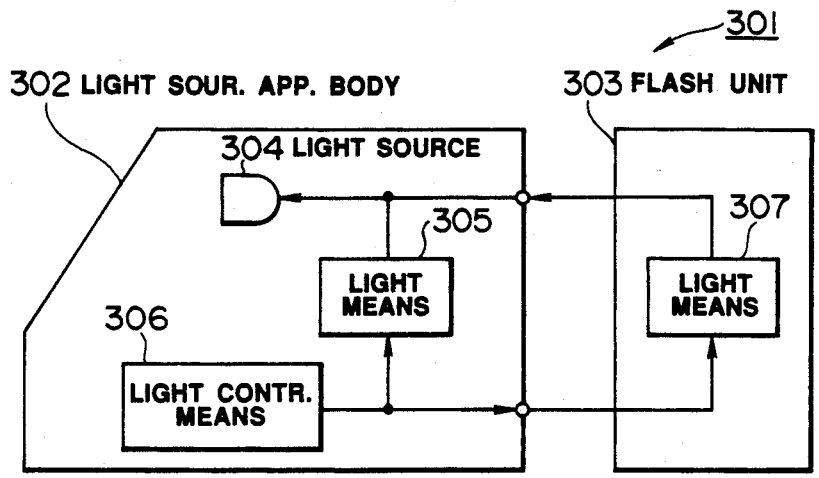
FIG. 22 is a schematic view of a light source apparatus, showing a seventh embodiment of the present invention.

FIG. 22 is a schematic view of a light source apparatus, showing a seventh embodiment of the present invention.

A light source apparatus 301 includes a light source apparatus body 302 and a flash unit 303 which can be detachably mounted on the light source apparatus body 302.

The light source apparatus body 302 includes a light source 304 which flashes when electric energy is supplied thereto, a lighting means 305 for supplying the electric energy which flashes the light source 304, and a lighting control means 306 for controlling the output of energy from the lighting means 305. The flash unit 303 that can be detachably mounted on the light source apparatus body 302 includes a lighting means 307. The lighting control means 306 also controls output of energy from the flash unit 303 to the light source 304.

Figure 23:
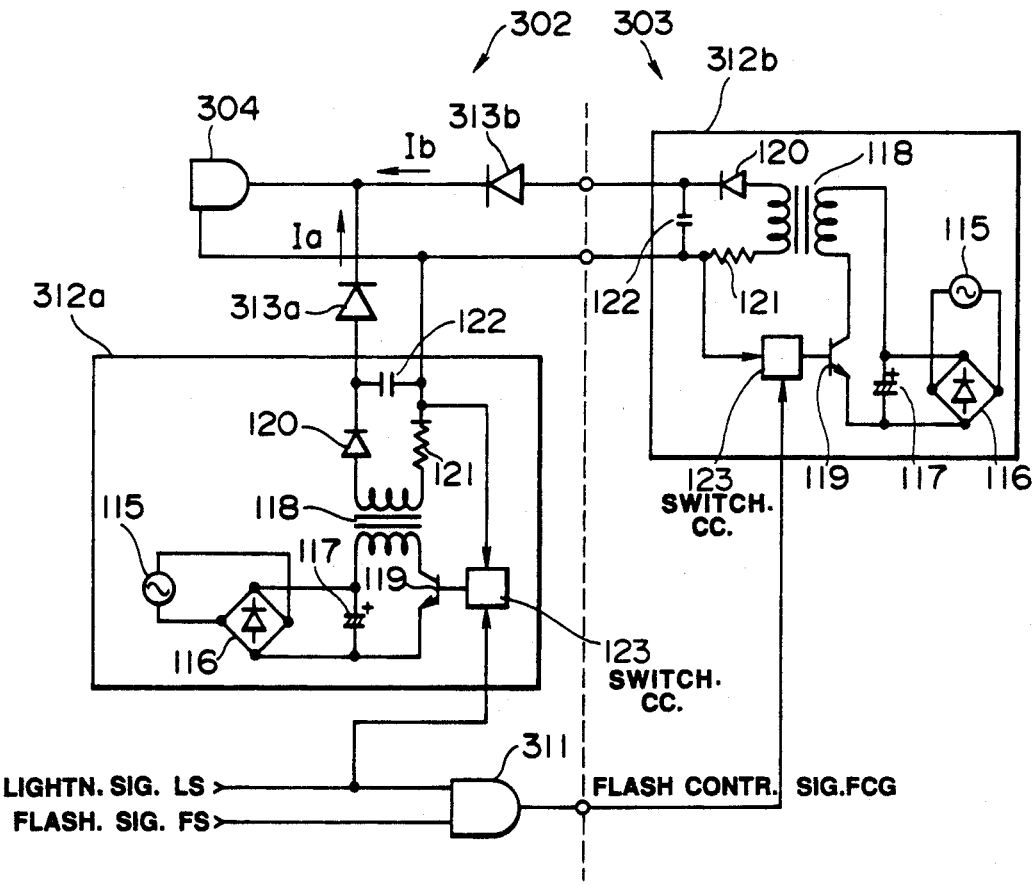
FIG. 23 is a circuit diagram showing the concrete configuration of the light source apparatus of FIG. 22.

FIG. 23 shows the concrete configuration of the electric system in the light source apparatus body 302 and that in the flash unit 303.

The light source apparatus body 302 has a lightening switch which is not shown. When this switch is turned on, a lighting signal LS is input to a AND gate 311 which constitutes the lighting control means 306 and to a switching power source 312a which constitutes the lighting means 305

To the AND gate 311 is also input a flash signal FS which is output by the releasing or freezing operation. A flash control signal FCS output from the AND gate 311 is input to a switching power source 312b which constitutes the lighting means 307 of the flash unit 303.

Positive output terminals of the switching power sources 312a and 312b are connected to an anode of the light source 304 through reverse current preventing diodes 313a and 313b, respectively, and negative output terminals thereof are connected to a cathode of the light source 304.

The switching power sources 312a and 312b have the same configuration. The same components are denoted by the same reference numerals.

Current from an alternating power source 415 is rectified by a diode bridge 416, and the rectified current is smoothed by a capacitor 417. The two ends of the capacitor 417 are series-connected to a switching transformer 418 and to a switching transistor 419. A secondary terminal of the transformer 418 is connected to a diode 420 and to a resistor 421 which are in turn connected to a capacitor 422. The connection between the capacitor 422 and the resistor 421 is connected to an input terminal of a switching circuit 423, and an output terminal of the switching circuit 423 is connected to a base of the transistor 419. A flash control signal FCS is applied from the AND gate 311 to a control terminal of the switching circuit 423. The switching circuit 423 outputs to the base of the transistor 419 a switching pulse when it receives the flash control signal FCS and thereby operates the transistor 419, by which the power supplied to the primary terminal of the transformer 418 is transferred to the secondary terminal thereof due to the electromagnetic induction. The induced current is smoothed by the diode 420 and the capacitor 422 and the smooth dc power is supplied to the light source 304.

Whereas the flashing energy supply means in the flash unit 26 in the first embodiment employs the large-capacitance capacitors, the flashing energy supply means in the flash unit 303 in the seventh embodiment employs the switching power sources.

The operation of the seventh embodiment of the present invention will be described below with reference to FIG. 24.

Figure 24A:
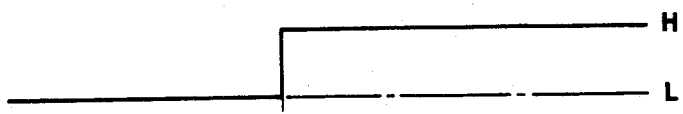
FIGS. 24a-24f explain the operation of the seventh embodiment.

When the lightening switch (not shown) of the light source apparatus body 302 is turned on, the lightening signal LS rises, as shown in FIG. 24a. In consequence, the switching circuit 423 in the switching power source 312a is operated and thus outputs a current Ia, as shown in FIG. 24d. The current Ia is used to obtain flashing at an intensity of light required for normal observation.

Figure 24B:
Figure 24C:
Figure 24D:
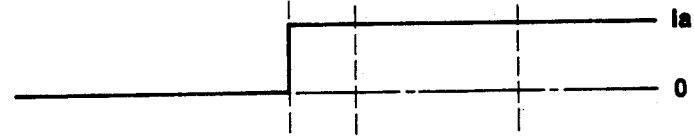
Figure 24E:
Figure 24F:

When the releasing switch is turned on in this state, a flash signal FS is generated, as shown in FIG. 24b, and supplied to the AND gate 311. This rises the flash control signal FCS shown in FIG. 24c. In the case where the flash unit 303 is connected to the light source apparatus body 302, the flash control signal FCS operates the switching circuit 420 in the switching power source 312b and the switching power source 312b thereby outputs a large current Ib, as shown in FIG. 24e. This large current Ib is superimposed with the current Ia output from the switching power source 312a, and the obtained current Ia+Ib shown in FIG. 24f is supplied to the light source 304 to increase the intensity of light at which the light source 304 flashes.

In this embodiment, the flashing output is more stable than that obtained in the case where the capacitors are used as the flashing power source. Furthermore, reduction in the flashing output which occurs when the releasing operation is conducted a large number of times is less, and less blurred still pictures can thus be obtained.

Figure 25:
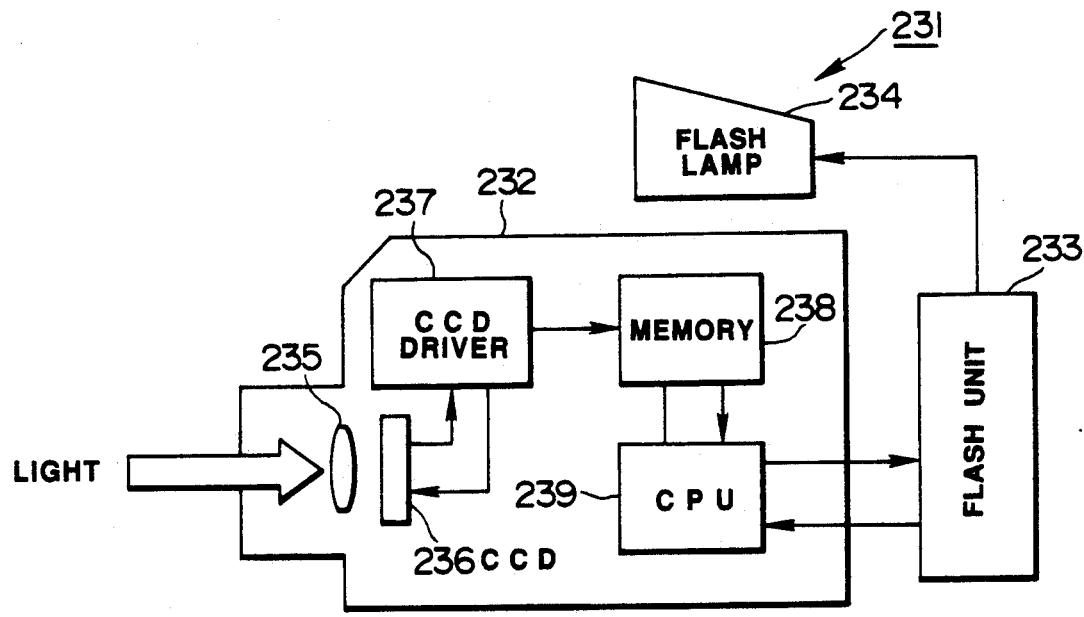
FIG. 25 is a schematic view of an imaging apparatus, showing an eighth embodiment of the present invention.

FIG. 25 shows an eighth embodiment of the present invention which is an imaging apparatus 231.

The imaging apparatus 231 includes a video camera 232, a flash unit 233 which can be detachably mounted on the video camera 232, and a flash lamp 234.

In the video camera 232, a CCD 236 is disposed on the focal point surface of an objective lens 235 to convert an optical image into an electrical signal. The electrical signal is read out from the CCD 236 and stored in a memory 238 by supply of a CCD drive signal (a CCD reading pulse) from a CCD driver 237. Write and read of data in and from the memory 238 is controlled by a CPU 239. The CPU 239 outputs a control signal to the flash unit 233 which drives the flash lamp 234 mounted on the video camera 232.

The operation of the eighth embodiment will be described below.

In the case where the flash unit 233 is not connected, when the freezing signal is output during the operation of the imaging apparatus in which external light is used for exposure, the electric charge of the CCD 236 is written in the memory 238 through the CCD driver 237 with a subsequent reading-out signal. Thereafter, writing in the memory 238 is inhibited by the CPU 239.

In the case where the flash unit 233 is connected, when the freezing signal is output, the pulse period is reduced by a subsequent pulse $\overline{DR}$. At the same time, the flash unit 233 receives a signal from the CPU 239 and flashes the flash lamp 234. At that time, the electric charge in the CCD 236 is read out from the CCD 236 by the CCD driver 237 and is accumulated in the memory 238 which is cleared when the freezing signal is output. Each time the electric charge is written in the memory 238, the total electric charge in each pixel is compared with the correct exposure. If the total electric charge is smaller than the correct exposure, accumulation of the electric charge continues. If the total electric charge is equal to the correct exposure, writing of the electric charge in the memory 238 is inhibited and flashing of the flash lamp 234 is suspended.

In the eighth embodiment of the present invention, since the shutter time can be reduced due to flashing, less blurred still pictures can be obtained.

It is possible to construct another embodiments by combining the above-described embodiments.

What is claimed is:

1. A light source apparatus for an endoscope, comprising:
a light source apparatus body including a light source which lights up and thereby supplies light to said endoscope, a lighting means for supplying energy required to light said light source, and a control means for controlling an operation of said lighting means; and
a flash unit including a connector means detachably connected to said light source apparatus body, and an energy supply means for supplying to said light source energy required to flash said light source.

2. A light source apparatus for an endoscope according to claim 1, wherein said endoscope comprises a fiber scope having an optical image transmission means constituted by a fiber bundle.

3. A light source apparatus for an endoscope according to claim 2, further comprising a TV camera with a solid imaging device incorporated therein, said TV camera being detachably mounted on said fiber scope.

4. A light source apparatus for an endoscope according to claim 1, wherein said endoscope comprises an electronic scope with a solid imaging device which converts an optical image into an electric signal.

5. A light source apparatus for an endoscope according to either of claims 3 or 4, further comprising a filter means disposed in an optical path of and in front of said light source to pass radiations with a plurality of wavelength bands in a white light emitted from said light source.

6. A light source apparatus for an endoscope according to either of claims 3 or 4, wherein said light source emits a white light.

7. A light source apparatus for an endoscope according to either of claims 3 or 4, further comprising a drive means for driving said solid-state imaging device, a signal processing means for conducting signal processing on an image signal which is output from said solid-state imaging device by the application of a drive signal output from said drive means thereto, and a monitor for displaying a standard video signal output from said signal processing means.

8. A light source apparatus for an endoscope according to claim 7, wherein said signal processing means includes an image signal storage means for temporarily storing said image signal.

9. A light source apparatus for an endoscope according to claim 8, wherein said image signal storage means is controlled on the basis of a freezing or releasing operation.

10. A light source apparatus for an endoscope according to claim 9, wherein said control means increases energy supplied from said lighting means to said light source on the basis of said freezing or releasing operation.

11. A light source apparatus for an endoscope according to claim 10, wherein said control means comprises a CPU.

12. A light source apparatus for an endoscope according to claim 9, wherein said control means controls said drive means such that it outputs said drive signal in short intervals on the basis of said freezing or releasing operation.

13. A light source apparatus for an endoscope according to claim 1, further comprising a connection detection means for detecting connection or disconnection of said flash unit.

14. A light source apparatus for an endoscope according to claim 13, wherein an output signal of said connection detection means is input to said control means, said control means controlling said energy supply means such that it supplies to said light source the energy required for flashing it when said flash unit is connected.

15. A light source apparatus for an endoscope according to claim 14, wherein said control means controls said drive means such that it outputs said drive signal in short intervals when flash unit is connected.

16. A light source apparatus for an endoscope according to claim 8, wherein said image signal storage means includes a still picture storage control means which stores a still picture by storing in said image signal storage means an image signal to be input to said image signal storage means in such a manner that it is added to an image signal stored in said image signal storage means until a level of said image signal reaches a reference value and then by inhibiting the storage.

17. A light source apparatus for an endoscope according to claim 1, wherein said flash unit includes a means for generating information signal corresponding to the magnitude of said flashing energy.

18. A light source apparatus for an endoscope according to claim 1, further comprising a shutter for blocking the light from said light source and a stop for controlling the amount of light which passes therethrough, said shutter and said stop being disposed in an optical path of and in front of said light source.

19. A light source apparatus for an endoscope according to claim 18, further comprising a second shutter whose response speed is faster than said shutter.

20. A light source apparatus for an endoscope according to claim 2, further comprising a still camera which can be detachably mounted on said fiber scope.

21. A light source apparatus for an endoscope according to claim 1, further comprising an attenuating filter for attenuating the intensity of light which passes therethrough, said attenuating filter being able to be disposed in an optical path of and in front of said light source.

22. A light source apparatus for an endoscope according to claim 7, further comprising an image file control means connected to said signal processing means to control recording of still pictures.

23. A light source apparatus for an endoscope according to claim 22, wherein said image file control means controls an operation of an image recording means connected to said image file control means to record still pictures.

24. A light source apparatus for an endoscope according to claim 23, wherein said image recording means comprises either an optical disk, an optical magnetic disk, VTR or a magnetic tape.

25. A light source apparatus for an endoscope according to claim 1, wherein said lighting means supplies energy required to continuously lighting said light source.

26. A light source apparatus for an endoscope according to claim 25, wherein said lighting means is also capable of supplying energy required to semi-flash said light source on the basis of said releasing or freezing operation.

27. A light source apparatus for an endoscope according to claim 26, wherein said lighting means includes a selection means which is capable of selecting between supply of the energy required to semi-flash said light source and supply of the energy required to continuously lightening said light source.

28. A light source apparatus for an endoscope according to claim 1, wherein said energy supply means of said flash unit comprises a switching regulator.

29. A light source apparatus for an endoscope according to claim 1, wherein said energy supply means of said flash unit comprises a capacitor having a capacitance.

30. A light source apparatus for an endoscope according to claim 1, wherein said control means has a plurality of sequences of control operations which are selectively conducted in accordance with connection of said flash unit.

31. A light source apparatus for an endoscope comprising:
a light source apparatus body including a light source which lights up and thereby supplies light to said endoscope, a lighting means for supplying energy required to light said light source, and a control means for controlling an operation of said lighting means;
a flash unit including a connector means detachably connected to said light source apparatus body, and an energy supply means for supplying to said light source energy required to flash said light source; and
a command means for outputting to said control means a command signal to flash said light source and for making said lighting means supply energy required to semi-flash said light source in such a manner that it is superimposed with said flashing energy.

32. A light source apparatus for an endoscope according to claim 31, wherein said command means outputs a releasing or freezing signal.

33. A light source apparatus comprising:
a light source apparatus body including a light source which emits light, a lighting means for supplying energy required to light said light source, and a control means for controlling an operation of said lighting means; and
a flash unit including a connector means detachably connected to said light source apparatus body, and an energy supply means for supplying to said light source energy required to flash said light source.

34. A light source apparatus for an endoscope according to claim 33, wherein said lighting means is capable of supplying energy required to semi-flash said light source on the basis of a releasing or freezing operation, and wherein said energy supply means supplies the energy required to flash said light source which is superimposed with said energy required to semi-flash said light source.

35. An endoscope system comprising:
an endoscope including an inserted portion, a light guide passed through said inserted portion to transmit light supplied to one of its end portions to the other end portion thereof and thereby illuminate an object, an objective optical system provided on a distal end of said inserted portion for forming an optical image, and an image transmission means for optically and electrically transmitting an image formed by said objective optical system;

a light source apparatus including a light source which lights up and thereby supplies light to said light guide, a lighting means for supplying energy required to light said light source, and a control means for controlling an operation of said lighting means; and flash unit including a connector means detachably connected to said light source apparatus, and a means for supplying to said light source energy required to flash said light source.

* * * * *